(12) United States Patent
Gertner

(10) Patent No.: US 8,715,209 B2
(45) Date of Patent: *May 6, 2014

(54) METHODS AND DEVICES TO MODULATE THE AUTONOMIC NERVOUS SYSTEM WITH ULTRASOUND

(75) Inventor: Michael Gertner, Menlo Park, CA (US)

(73) Assignee: Kona Medical, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/445,903

(22) Filed: Apr. 12, 2012

(65) Prior Publication Data

US 2012/0197166 A1    Aug. 2, 2012

Related U.S. Application Data

(63) Continuation of application No. 12/685,655, filed on Jan. 11, 2010, now Pat. No. 8,295,912.

(60) Provisional application No. 61/256,983, filed on Oct. 31, 2009, provisional application No. 61/250,857, filed on Oct. 12, 2009, provisional application No. 61/261,741, filed on Nov. 16, 2009, provisional application No. 61/291,359, filed on Dec. 30, 2009.

(51) Int. Cl.
    *A61B 5/05*    (2006.01)

(52) U.S. Cl.
    USPC ........ 601/2; 601/3; 601/4; 600/407; 600/424; 600/437

(58) Field of Classification Search
    USPC .................................. 600/407–475; 601/2–4
    See application file for complete search history.

(56) References Cited

U.S. PATENT DOCUMENTS

| | | |
|---|---|---|
| 385,256 A | 6/1888 | Eggers |
| 3,274,437 A | 9/1966 | Mastrup |
| 3,499,437 A | 3/1970 | Balamuth |
| 3,552,382 A | 1/1971 | Mount |
| 3,847,016 A | 11/1974 | Ziedonis |
| 3,927,662 A | 12/1975 | Ziedonis |
| 4,059,098 A | 11/1977 | Murdock |
| 4,167,180 A | 9/1979 | Kossoff |
| 4,197,856 A | 4/1980 | Northrop |
| 4,206,763 A | 6/1980 | Pendersen |

(Continued)

FOREIGN PATENT DOCUMENTS

| | | |
|---|---|---|
| EP | 0225120 A2 | 6/1987 |
| EP | 0420758 A1 | 4/1991 |

(Continued)

OTHER PUBLICATIONS

Advisory Action dated Jun. 29, 2012 for U.S. Appl. No. 13/246,763.

(Continued)

*Primary Examiner* — Tse Chen
*Assistant Examiner* — Mark Remaly
(74) *Attorney, Agent, or Firm* — Morrison & Foerster LLP

(57) ABSTRACT

In some embodiments, sympathetic nerves surrounding arteries or leading to organs are targeted with energy sources to correct or modulate physiologic processes. In some embodiments, different types of energy sources are utilized singly or combined with one another. In some embodiments, bioactive agents or devices activated by the energy sources are delivered to the region of interest and the energy is enhanced by such agents.

29 Claims, 27 Drawing Sheets

(56) References Cited

U.S. PATENT DOCUMENTS

| | | |
|---|---|---|
| 4,237,901 A | 12/1980 | Taenzer |
| 4,273,127 A | 6/1981 | Auth et al. |
| 4,469,099 A | 9/1984 | McEwen |
| 4,479,494 A | 10/1984 | McEwen |
| 4,484,569 A | 11/1984 | Driller et al. |
| 4,545,386 A | 10/1985 | Hetz et al. |
| 4,601,296 A | 7/1986 | Yerushalmi |
| 4,605,010 A | 8/1986 | McEwen |
| 4,688,578 A | 8/1987 | Takano et al. |
| 4,708,836 A | 11/1987 | Gain et al. |
| 4,748,985 A | 6/1988 | Nagasaki |
| 4,757,820 A | 7/1988 | Itoh |
| 4,770,175 A | 9/1988 | McEwen |
| 4,773,865 A | 9/1988 | Baldwin |
| 4,784,148 A | 11/1988 | Dow et al. |
| 4,841,979 A | 6/1989 | Dow et al. |
| 4,850,363 A | 7/1989 | Yanagawa |
| 4,858,613 A | 8/1989 | Fry et al. |
| 4,905,672 A | 3/1990 | Schwarze et al. |
| 4,913,155 A | 4/1990 | Dow et al. |
| 4,929,246 A | 5/1990 | Sinofsky |
| 4,931,047 A | 6/1990 | Broadwin et al. |
| 4,938,216 A | 7/1990 | Lele |
| 4,938,217 A | 7/1990 | Lele |
| 4,957,099 A | 9/1990 | Hassler |
| 5,005,579 A | 4/1991 | Wurster et al. |
| RE33,590 E | 5/1991 | Dory |
| 5,026,387 A | 6/1991 | Thomas |
| 5,036,855 A | 8/1991 | Fry et al. |
| 5,039,774 A | 8/1991 | Shikinami et al. |
| 5,042,486 A | 8/1991 | Pfeiler et al. |
| 5,065,742 A | 11/1991 | Belikan et al. |
| 5,080,101 A | 1/1992 | Dory |
| 5,080,102 A | 1/1992 | Dory |
| 5,150,712 A | 9/1992 | Dory |
| 5,170,790 A | 12/1992 | Lacoste et al. |
| 5,178,135 A | 1/1993 | Uchiyama et al. |
| 5,178,148 A | 1/1993 | Lacoste et al. |
| 5,181,522 A | 1/1993 | McEwen |
| 5,193,527 A | 3/1993 | Schafer |
| 5,194,291 A | 3/1993 | D'Aoust et al. |
| 5,211,160 A | 5/1993 | Talish et al. |
| 5,215,680 A | 6/1993 | D'Arrigo |
| 5,219,401 A | 6/1993 | Cathignol et al. |
| 5,230,334 A | 7/1993 | Klopotek |
| 5,230,921 A | 7/1993 | Waltonen et al. |
| 5,233,994 A | 8/1993 | Shmulewitz |
| 5,243,988 A | 9/1993 | Sieben et al. |
| 5,254,087 A | 10/1993 | McEwen |
| 5,263,957 A | 11/1993 | Davison |
| 5,290,278 A | 3/1994 | Anderson |
| 5,311,869 A | 5/1994 | Okazaki |
| 5,312,431 A | 5/1994 | McEwen |
| 5,352,195 A | 10/1994 | McEwen |
| 5,364,389 A | 11/1994 | Anderson |
| 5,383,896 A | 1/1995 | Gershony et al. |
| 5,391,140 A | 2/1995 | Schaetzle et al. |
| 5,391,197 A | 2/1995 | Burdette et al. |
| 5,394,877 A | 3/1995 | Orr et al. |
| 5,413,550 A | 5/1995 | Castel |
| 5,415,657 A | 5/1995 | Taymor-Luria |
| 5,439,477 A | 8/1995 | McEwen |
| 5,453,576 A | 9/1995 | Krivitski |
| 5,454,373 A | 10/1995 | Koger et al. |
| 5,454,831 A | 10/1995 | McEwen |
| 5,471,988 A | 12/1995 | Fujio et al. |
| 5,474,071 A | 12/1995 | Chapelon et al. |
| 5,492,126 A | 2/1996 | Hennige et al. |
| 5,503,152 A | 4/1996 | Oakley et al. |
| 5,507,744 A | 4/1996 | Tay et al. |
| 5,507,790 A | 4/1996 | Weiss |
| 5,515,853 A | 5/1996 | Smith et al. |
| 5,520,188 A | 5/1996 | Hennige et al. |
| 5,522,878 A | 6/1996 | Montecalvo et al. |
| 5,524,620 A | 6/1996 | Rosenschein |
| 5,526,815 A | 6/1996 | Granz et al. |
| 5,534,232 A | 7/1996 | Denes et al. |
| 5,536,489 A | 7/1996 | Lohrmann et al. |
| 5,553,618 A | 9/1996 | Suzuki et al. |
| 5,556,415 A | 9/1996 | McEwen et al. |
| 5,558,092 A | 9/1996 | Unger et al. |
| 5,573,497 A | 11/1996 | Chapelon |
| 5,578,055 A | 11/1996 | McEwen |
| 5,584,853 A | 12/1996 | McEwen |
| 5,601,526 A | 2/1997 | Chapelon et al. |
| 5,607,447 A | 3/1997 | McEwen et al. |
| 5,609,485 A | 3/1997 | Bergman et al. |
| 5,626,601 A | 5/1997 | Gershony et al. |
| 5,630,837 A | 5/1997 | Crowley |
| 5,638,823 A | 6/1997 | Akay et al. |
| 5,643,179 A | 7/1997 | Fujimoto |
| 5,649,954 A | 7/1997 | McEwen |
| 5,655,538 A | 8/1997 | Lorraine et al. |
| 5,657,760 A | 8/1997 | Ying et al. |
| 5,665,073 A | 9/1997 | Bulow et al. |
| 5,666,954 A | 9/1997 | Chapelon et al. |
| 5,681,339 A | 10/1997 | McEwen et al. |
| 5,685,307 A | 11/1997 | Holland et al. |
| 5,695,493 A | 12/1997 | Nakajima et al. |
| 5,697,897 A | 12/1997 | Buchholtz et al. |
| D389,574 S | 1/1998 | Emerson et al. |
| 5,711,058 A | 1/1998 | Frey et al. |
| 5,716,374 A | 2/1998 | Francese et al. |
| 5,720,286 A | 2/1998 | Chapelon et al. |
| 5,720,287 A | 2/1998 | Chapelon et al. |
| 5,722,411 A | 3/1998 | Suzuki |
| 5,726,066 A | 3/1998 | Choi |
| 5,735,796 A | 4/1998 | Granz et al. |
| 5,738,635 A | 4/1998 | Chapelon et al. |
| 5,741,295 A | 4/1998 | McEwen |
| 5,755,228 A | 5/1998 | Wilson et al. |
| 5,762,066 A | 6/1998 | Law et al. |
| 5,769,790 A | 6/1998 | Watkins et al. |
| 5,788,636 A | 8/1998 | Curley |
| 5,807,285 A | 9/1998 | Vaitekunas |
| 5,810,007 A | 9/1998 | Holupka et al. |
| 5,810,810 A | 9/1998 | Tay et al. |
| 5,817,021 A | 10/1998 | Reichenberger |
| 5,823,962 A | 10/1998 | Schaetzle et al. |
| 5,824,015 A | 10/1998 | Sawyer |
| 5,824,277 A | 10/1998 | Campos |
| 5,827,204 A | 10/1998 | Grandia et al. |
| 5,827,268 A | 10/1998 | Laufer |
| 5,833,647 A | 11/1998 | Edwards |
| 5,840,028 A | 11/1998 | Chubachi et al. |
| 5,846,517 A | 12/1998 | Unger |
| 5,852,860 A | 12/1998 | Lorraine et al. |
| 5,853,752 A | 12/1998 | Unger et al. |
| 5,855,589 A | 1/1999 | McEwen et al. |
| 5,873,828 A | 2/1999 | Fujio et al. |
| 5,873,845 A | 2/1999 | Cline et al. |
| 5,879,314 A | 3/1999 | Peterson et al. |
| 5,882,302 A | 3/1999 | Driscoll, Jr. et al. |
| 5,895,356 A | 4/1999 | Andrus et al. |
| 5,904,659 A | 5/1999 | Duarte et al. |
| 5,906,580 A | 5/1999 | Kline-Schoder et al. |
| 5,911,735 A | 6/1999 | McEwen |
| 5,919,139 A | 7/1999 | Lin |
| 5,921,994 A | 7/1999 | Andreas et al. |
| 5,922,945 A | 7/1999 | Allmaras et al. |
| 5,931,786 A | 8/1999 | Whitmore, III et al. |
| 5,931,853 A | 8/1999 | McEwen |
| 5,935,144 A | 8/1999 | Estabrook |
| 5,935,146 A | 8/1999 | McEwen |
| 5,935,339 A | 8/1999 | Henderson et al. |
| 5,938,600 A | 8/1999 | Van Vaals et al. |
| 5,951,476 A | 9/1999 | Beach |
| 5,957,849 A | 9/1999 | Munro |
| 5,964,782 A | 10/1999 | Lafontaine et al. |
| 5,976,092 A | 11/1999 | Chinn |
| 5,979,453 A | 11/1999 | Savage et al. |
| 5,993,389 A | 11/1999 | Driscoll, Jr. et al. |
| 5,997,481 A | 12/1999 | Adams et al. |
| 6,007,499 A | 12/1999 | Martin et al. |

(56) References Cited

U.S. PATENT DOCUMENTS

| | | |
|---|---|---|
| 6,014,473 A | 1/2000 | Hossack et al. |
| 6,033,506 A | 3/2000 | Klett |
| 6,036,650 A | 3/2000 | Wu et al. |
| 6,037,032 A | 3/2000 | Klett et al. |
| 6,039,694 A | 3/2000 | Larson et al. |
| 6,050,943 A | 4/2000 | Slayton et al. |
| 6,067,371 A | 5/2000 | Gouge et al. |
| 6,068,596 A | 5/2000 | Weth et al. |
| 6,071,239 A | 6/2000 | Cribbs et al. |
| 6,071,277 A | 6/2000 | Farley et al. |
| 6,078,831 A | 6/2000 | Belef et al. |
| 6,083,159 A | 7/2000 | Driscoll, Jr. et al. |
| 6,087,761 A | 7/2000 | Lorraine et al. |
| 6,102,860 A | 8/2000 | Mooney |
| 6,106,463 A | 8/2000 | Wilk |
| 6,120,453 A | 9/2000 | Sharp |
| 6,128,522 A | 10/2000 | Acker et al. |
| 6,179,831 B1 | 1/2001 | Bliweis |
| 6,182,341 B1 | 2/2001 | Talbot et al. |
| 6,200,539 B1 | 3/2001 | Sherman et al. |
| 6,206,843 B1 | 3/2001 | Iger et al. |
| 6,213,939 B1 | 4/2001 | McEwen |
| 6,217,530 B1 | 4/2001 | Martin et al. |
| 6,221,015 B1 | 4/2001 | Yock |
| 6,231,507 B1 | 5/2001 | Zikorus et al. |
| 6,233,477 B1 | 5/2001 | Chia et al. |
| 6,246,156 B1 | 6/2001 | Takeuchi et al. |
| 6,254,601 B1 | 7/2001 | Burbank et al. |
| 6,259,945 B1 | 7/2001 | Epstein et al. |
| 6,263,551 B1 | 7/2001 | Lorraine et al. |
| 6,267,734 B1 | 7/2001 | Ishibashi et al. |
| 6,270,458 B1 | 8/2001 | Barnea |
| 6,277,077 B1 | 8/2001 | Brisken et al. |
| 6,315,441 B2 | 11/2001 | King |
| 6,332,089 B1 | 12/2001 | Acker et al. |
| 6,361,496 B1 | 3/2002 | Zikorus et al. |
| 6,361,548 B1 | 3/2002 | McEwen |
| 6,399,149 B1 | 6/2002 | Klett et al. |
| 6,406,759 B1 | 6/2002 | Roth |
| 6,409,720 B1 | 6/2002 | Hissong et al. |
| 6,419,669 B1 | 7/2002 | Frazier et al. |
| 6,425,867 B1 | 7/2002 | Vaezy et al. |
| 6,425,876 B1 | 7/2002 | Frangi et al. |
| 6,432,067 B1 | 8/2002 | Martin et al. |
| 6,443,894 B1 | 9/2002 | Sumanaweera et al. |
| 6,453,526 B2 | 9/2002 | Lorraine et al. |
| 6,488,639 B1 | 12/2002 | Ribault et al. |
| 6,491,672 B2 | 12/2002 | Slepian et al. |
| 6,494,848 B1 | 12/2002 | Sommercorn et al. |
| 6,500,133 B2 | 12/2002 | Martin et al. |
| 6,506,171 B1 | 1/2003 | Vitek et al. |
| 6,514,221 B2 | 2/2003 | Hynynen et al. |
| 6,520,915 B1 | 2/2003 | Lin et al. |
| 6,522,926 B1 | 2/2003 | Kieval et al. |
| 6,548,047 B1 | 4/2003 | Unger |
| 6,551,576 B1 | 4/2003 | Unger et al. |
| 6,559,644 B2 | 5/2003 | Froundlich et al. |
| 6,562,037 B2 | 5/2003 | Paton et al. |
| 6,565,557 B1 | 5/2003 | Sporri et al. |
| 6,576,168 B2 | 6/2003 | Hardcastle et al. |
| 6,584,360 B2 | 6/2003 | Francischelli et al. |
| 6,595,934 B1 | 7/2003 | Hissong et al. |
| 6,599,256 B1 | 7/2003 | Acker et al. |
| 6,599,288 B2 | 7/2003 | Maguire |
| 6,602,251 B2 | 8/2003 | Burbank et al. |
| 6,612,988 B2 | 9/2003 | Maor et al. |
| 6,616,624 B1 | 9/2003 | Kieval |
| 6,626,855 B1 | 9/2003 | Weng et al. |
| 6,633,658 B1 | 10/2003 | Dabney et al. |
| 6,652,461 B1 | 11/2003 | Levkovitz |
| 6,656,131 B2 | 12/2003 | Alster et al. |
| 6,656,136 B1 | 12/2003 | Weng et al. |
| 6,676,601 B1 | 1/2004 | Lacoste et al. |
| 6,682,483 B1 | 1/2004 | Abend et al. |
| 6,685,639 B1 | 2/2004 | Wang et al. |
| 6,706,892 B1 | 3/2004 | Ezrin et al. |
| 6,709,392 B1 | 3/2004 | Salgo et al. |
| 6,709,407 B2 | 3/2004 | Fatemi |
| 6,716,184 B2 | 4/2004 | Vaezy et al. |
| 6,719,694 B2 | 4/2004 | Weng et al. |
| 6,719,699 B2 | 4/2004 | Smith |
| 6,726,627 B1 | 4/2004 | Lizzi et al. |
| 6,735,461 B2 | 5/2004 | Vitek et al. |
| 6,755,789 B2 | 6/2004 | Stringer et al. |
| 6,764,488 B1 | 7/2004 | Burbank et al. |
| 6,846,291 B2 | 1/2005 | Smith et al. |
| 6,875,176 B2 | 4/2005 | Mourad et al. |
| 6,875,420 B1 | 4/2005 | Quay |
| 6,905,498 B2 | 6/2005 | Hooven |
| 6,932,771 B2 | 8/2005 | Whitmore et al. |
| 6,955,648 B2 | 10/2005 | Mozayeni et al. |
| 6,978,174 B2 | 12/2005 | Gelfand et al. |
| 7,022,077 B2 | 4/2006 | Mourad et al. |
| 7,052,463 B2 | 5/2006 | Peszynski et al. |
| 7,063,666 B2 | 6/2006 | Weng et al. |
| 7,128,711 B2 | 10/2006 | Medan et al. |
| 7,149,564 B2 | 12/2006 | Vining et al. |
| 7,162,303 B2 | 1/2007 | Levin et al. |
| 7,211,060 B1 | 5/2007 | Talish et al. |
| 7,260,250 B2 | 8/2007 | Summers et al. |
| 7,285,093 B2 | 10/2007 | Anisimov et al. |
| 7,445,599 B2 | 11/2008 | Kelly et al. |
| 7,470,241 B2 | 12/2008 | Weng et al. |
| 7,499,748 B2 | 3/2009 | Moffitt et al. |
| 7,510,536 B2 | 3/2009 | Foley et al. |
| 7,530,958 B2 | 5/2009 | Slayton et al. |
| 7,534,209 B2 | 5/2009 | Abend |
| 7,553,284 B2 | 6/2009 | Vaitekunas |
| 7,617,005 B2 | 11/2009 | Demarais et al. |
| 7,620,451 B2 | 11/2009 | Demarais et al. |
| 7,628,764 B2 | 12/2009 | Duarte et al. |
| 7,684,865 B2 | 3/2010 | Aldrich et al. |
| 7,697,972 B2 | 4/2010 | Verard et al. |
| 7,783,358 B2 | 8/2010 | Aldrich et al. |
| 8,295,912 B2 | 10/2012 | Gertner |
| 8,347,891 B2 | 1/2013 | Demarais et al. |
| 2001/0014775 A1 | 8/2001 | Koger et al. |
| 2001/0014805 A1 | 8/2001 | Burbank et al. |
| 2001/0032382 A1 | 10/2001 | Lorraine et al. |
| 2001/0041910 A1 | 11/2001 | McEwen |
| 2001/0044636 A1 | 11/2001 | Pedros et al. |
| 2002/0055736 A1 | 5/2002 | Horn et al. |
| 2002/0072672 A1 | 6/2002 | Roundhill et al. |
| 2002/0095164 A1 | 7/2002 | Andreas et al. |
| 2002/0193831 A1 | 12/2002 | Smith, III |
| 2003/0009194 A1 | 1/2003 | Saker et al. |
| 2003/0018255 A1 | 1/2003 | Martin et al. |
| 2003/0036771 A1 | 2/2003 | McEwen |
| 2003/0050665 A1 | 3/2003 | Ginn |
| 2003/0069569 A1 | 4/2003 | Burdette et al. |
| 2003/0114756 A1 | 6/2003 | Li |
| 2003/0120204 A1 | 6/2003 | Unger et al. |
| 2003/0153849 A1 | 8/2003 | Huckle et al. |
| 2003/0195420 A1 | 10/2003 | Mendlein et al. |
| 2003/0208101 A1 | 11/2003 | Cecchi |
| 2003/0216792 A1 | 11/2003 | Levin et al. |
| 2004/0002654 A1 | 1/2004 | Davidson et al. |
| 2004/0030227 A1 | 2/2004 | Littrup et al. |
| 2004/0030268 A1 | 2/2004 | Weng et al. |
| 2004/0030269 A1 | 2/2004 | Horn et al. |
| 2004/0039280 A1* | 2/2004 | Wu et al. ........................ 600/412 |
| 2004/0054287 A1 | 3/2004 | Stephens |
| 2004/0054289 A1 | 3/2004 | Eberle et al. |
| 2004/0078034 A1 | 4/2004 | Acker et al. |
| 2004/0078219 A1 | 4/2004 | Kaylor et al. |
| 2004/0082978 A1 | 4/2004 | Harrison et al. |
| 2004/0097805 A1 | 5/2004 | Verard et al. |
| 2004/0097840 A1 | 5/2004 | Holmer |
| 2004/0106880 A1 | 6/2004 | Weng et al. |
| 2004/0113524 A1 | 6/2004 | Baumgartner et al. |
| 2004/0122493 A1 | 6/2004 | Ishibashi et al. |
| 2004/0127798 A1 | 7/2004 | Dala-Krishna et al. |
| 2004/0153126 A1 | 8/2004 | Okai |
| 2004/0158154 A1 | 8/2004 | Hanafy et al. |

(56) References Cited

U.S. PATENT DOCUMENTS

| | | |
|---|---|---|
| 2004/0220167 A1 | 11/2004 | Samly |
| 2004/0234453 A1 | 11/2004 | Smith |
| 2004/0254620 A1 | 12/2004 | Lacoste et al. |
| 2004/0267252 A1 | 12/2004 | Washington et al. |
| 2005/0043625 A1 | 2/2005 | Oliver et al. |
| 2005/0046311 A1 | 3/2005 | Baumgartner et al. |
| 2005/0054955 A1 | 3/2005 | Lidgren |
| 2005/0065436 A1 | 3/2005 | Ho et al. |
| 2005/0070790 A1 | 3/2005 | Niwa et al. |
| 2005/0085793 A1 | 4/2005 | Glossop |
| 2005/0090104 A1 | 4/2005 | Yang et al. |
| 2005/0096538 A1 | 5/2005 | Chomas et al. |
| 2005/0096542 A1 | 5/2005 | Weng et al. |
| 2005/0154299 A1 | 7/2005 | Hoctor et al. |
| 2005/0165298 A1 | 7/2005 | Larson et al. |
| 2005/0182297 A1 | 8/2005 | Gravenstein et al. |
| 2005/0182319 A1 | 8/2005 | Glossop |
| 2005/0192638 A1 | 9/2005 | Gelfand et al. |
| 2005/0240102 A1 | 10/2005 | Rachlin et al. |
| 2005/0240103 A1 | 10/2005 | Byrd et al. |
| 2005/0240126 A1 | 10/2005 | Foley et al. |
| 2005/0240127 A1 | 10/2005 | Seip et al. |
| 2005/0240170 A1 | 10/2005 | Zhang et al. |
| 2005/0240241 A1* | 10/2005 | Yun et al. ................ 607/42 |
| 2005/0288730 A1* | 12/2005 | Deem et al. ................ 607/42 |
| 2006/0025756 A1 | 2/2006 | Francischelli et al. |
| 2006/0052701 A1 | 3/2006 | Carter et al. |
| 2006/0058678 A1 | 3/2006 | Vitek et al. |
| 2006/0122514 A1 | 6/2006 | Byrd et al. |
| 2006/0184069 A1 | 8/2006 | Vaitekunas |
| 2006/0235300 A1 | 10/2006 | Weng et al. |
| 2007/0004984 A1 | 1/2007 | Crum et al. |
| 2007/0038115 A1 | 2/2007 | Quigley et al. |
| 2007/0055155 A1 | 3/2007 | Owen et al. |
| 2007/0106339 A1 | 5/2007 | Errico et al. |
| 2007/0129720 A1 | 6/2007 | Demarais et al. |
| 2007/0129761 A1 | 6/2007 | Demarais et al. |
| 2007/0135875 A1 | 6/2007 | Demarais et al. |
| 2007/0142879 A1 | 6/2007 | Greenberg et al. |
| 2007/0149880 A1 | 6/2007 | Willis |
| 2007/0167806 A1 | 7/2007 | Wood et al. |
| 2007/0179379 A1 | 8/2007 | Weng et al. |
| 2007/0213616 A1 | 9/2007 | Anderson et al. |
| 2007/0233185 A1 | 10/2007 | Anderson et al. |
| 2007/0239000 A1 | 10/2007 | Emery et al. |
| 2007/0265687 A1 | 11/2007 | Deem et al. |
| 2008/0033292 A1 | 2/2008 | Shafran |
| 2008/0033420 A1 | 2/2008 | Nields et al. |
| 2008/0039746 A1 | 2/2008 | Hissong et al. |
| 2008/0045864 A1 | 2/2008 | Candy et al. |
| 2008/0045865 A1 | 2/2008 | Kislev |
| 2008/0047325 A1 | 2/2008 | Bartlett |
| 2008/0058683 A1 | 3/2008 | Gifford et al. |
| 2008/0200806 A1 | 8/2008 | Liu et al. |
| 2008/0200815 A1 | 8/2008 | Van Der Steen et al. |
| 2008/0234569 A1 | 9/2008 | Tidhar et al. |
| 2008/0255498 A1 | 10/2008 | Houle |
| 2008/0255642 A1 | 10/2008 | Demarais et al. |
| 2008/0312561 A1 | 12/2008 | Chauhan |
| 2008/0312562 A1 | 12/2008 | Routh et al. |
| 2008/0317204 A1 | 12/2008 | Sumanaweera et al. |
| 2008/0319375 A1 | 12/2008 | Hardy |
| 2009/0012098 A1 | 1/2009 | Jordan et al. |
| 2009/0036948 A1 | 2/2009 | Levin et al. |
| 2009/0054770 A1 | 2/2009 | Daigle |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0088623 A1 | 4/2009 | Vortman et al. |
| 2009/0112095 A1 | 4/2009 | Daigle |
| 2009/0112133 A1 | 4/2009 | Deisseroth et al. |
| 2009/0163982 A1 | 6/2009 | Decharms |
| 2009/0221908 A1 | 9/2009 | Glossop |
| 2009/0221939 A1 | 9/2009 | Demarais et al. |
| 2009/0247911 A1 | 10/2009 | Novak et al. |
| 2009/0264755 A1 | 10/2009 | Chen et al. |
| 2009/0306644 A1 | 12/2009 | Mayse et al. |
| 2010/0022921 A1 | 1/2010 | Seip et al. |
| 2010/0023088 A1* | 1/2010 | Stack et al. ................ 607/44 |
| 2010/0042020 A1 | 2/2010 | Ben-Ezra |
| 2010/0092424 A1 | 4/2010 | Sanghvi et al. |
| 2010/0125269 A1 | 5/2010 | Emmons et al. |
| 2010/0160781 A1 | 6/2010 | Carter et al. |
| 2010/0174188 A1 | 7/2010 | Wang et al. |
| 2011/0028867 A1 | 2/2011 | Choo et al. |
| 2011/0112400 A1 | 5/2011 | Emery et al. |

FOREIGN PATENT DOCUMENTS

| | | |
|---|---|---|
| EP | 0679371 A1 | 11/1995 |
| EP | 1265223 A2 | 12/2002 |
| EP | 1579889 | 9/2005 |
| EP | 1 847 294 A1 | 10/2007 |
| EP | 1847294 A1 | 10/2007 |
| WO | WO 9731364 A1 | 8/1997 |
| WO | WO 9948621 A2 | 9/1999 |
| WO | WO-2011/046880 A3 | 4/2001 |
| WO | WO 0134018 A2 | 5/2001 |
| WO | WO 0269805 A2 | 9/2002 |
| WO | WO 2005030295 A2 | 4/2005 |
| WO | WO 2006129099 | 12/2006 |
| WO | WO 2008144274 | 11/2008 |
| WO | WO 2009018351 | 2/2009 |
| WO | WO 2009018394 A1 | 2/2009 |
| WO | WO-2011/046879 A1 | 4/2011 |
| WO | WO-2011/046880 A2 | 4/2011 |
| WO | WO 2011053757 A1 | 5/2011 |
| WO | WO 2011053772 A1 | 5/2011 |
| WO | WO-2012/125172 A1 | 9/2012 |

OTHER PUBLICATIONS

Advisory Action dated Jul. 9, 2012 for U.S. Appl. No. 12/685,655.
Final Office Action dated Aug. 29, 2012 for U.S. Appl. No. 12/966,954.
Final Office Action dated Jun. 26, 2012 for U.S. Appl. No. 12/685,655.
Non-Final Office Action dated Aug. 29, 2012 for U.S. Appl. No. 13/487,118.
Non-Final Office Action dated Aug. 29, 2012 for U.S. Appl. No. 13/487,121.
Non-Final Office Action dated Jul. 27, 2012 for U.S. Appl. No. 13/487,135.
Non-Final Office Action dated Jul. 3, 2012 for U.S. Appl. No. 12/902,133.
Non-Final Office Action dated Jun. 18, 2012 for U.S. Appl. No. 12/966,954.
Non-Final Office Action dated Jun. 18, 2012 for U.S. Appl. No. 12/966,962.
Non-Final Office Action dated Jun. 22, 2012 for U.S. Appl. No. 12/966,943.
Non-Final Office Action dated Jun. 8, 2012 for U.S. Appl. No. 13/019,273.
Notice of Allowance dated Aug. 27, 2012 for U.S. Appl. No. 12/685,655.
Advisory Action mailed on Feb. 25, 2013 for U.S. Appl. No. 13/487,135, filed Jun. 1, 2012, three pages.
Advisory Action mailed on Dec. 28, 2012 for U.S. Appl. No. 13/246,775, filed Sep. 27, 2011, three pages.
Advisory Action mailed on Aug. 15, 2012 for U.S. Appl. No. 12/725,450, filed Mar. 16, 2010, two pages.
European Examination Report mailed on Oct. 22, 2012 for EP Patent Application No. 10810835.8, four pages.
Extended European Search Report mailed on Dec. 7, 2012 for EP Patent Application No. 11758075.3, six pages.
Extended European Search Report mailed on Oct. 22, 2012 for EP Patent Application No. 10823909.6, eight pages.
Final Office Action mailed on Mar. 15, 2013 for U.S. Appl. No. 13/111,837, filed May 19, 2011, seven pages.

(56) References Cited

OTHER PUBLICATIONS

Final Office Action mailed on Mar. 14, 2013 for U.S. Appl. No. 13/091,116, filed Apr. 20, 2011, six pages.
Final Office Action mailed on Feb. 25, 2013 for U.S. Appl. No. 13/048,842, filed Mar. 15, 2011, seven pages.
Final Office Action mailed on Feb. 15, 2013 for U.S. Appl. No. 13/048,830, filed Mar. 15, 2011, six pages.
Final Office Action mailed on Feb. 1, 2013 for U.S. Appl. No. 13/523,835, filed Jun. 14, 2012, seven pages.
Final Office Action mailed on Jan. 31, 2013 for U.S. Appl. No. 13/535,070, filed Jun. 27, 2012, seven pages.
Final Office Action mailed on Jan. 29, 2013 for U.S. Appl. No. 13/048,837, filed Mar. 15, 2011, eight pages.
Final Office Action mailed on Jan. 17, 2013 for U.S. Appl. No. 13/487,118, filed Jun. 1, 2012, seven pages.
Final Office Action mailed on Jan. 15, 2013 for U.S. Appl. No. 13/487,121, filed Jun. 1, 2012, nine pages.
Final Office Action mailed on Dec. 10, 2012 for U.S. Appl. No. 12/966,962, filed Dec. 13, 2010, seven pages.
Final Office Action mailed on Dec. 5, 2012 for U.S. Appl. No. 12/966,943, filed Dec. 13, 2010, seven pages.
Final Office Action mailed on Dec. 4, 2012 for U.S. Appl. No. 13/487,135, filed Jun. 1, 2012, nine pages.
Final Office Action mailed on Oct. 23, 2012 for U.S. Appl. No. 13/019,273, filed Feb. 1, 2011, seven pages.
Final Office Action mailed on Oct. 16, 2012 for U.S. Appl. No. 13/246,775, filed Sep. 27, 2011, 17 pages.
Final Office Action mailed on Jun. 6, 2012 for U.S. Appl. No. 12/725,450, filed Mar. 16, 2010, ten pages.
Non-Final Office Action mailed on Jan. 2, 2013 for U.S. Appl. No. 13/545,944, filed Jul. 10, 2012, eight pages.
Non-Final Office Action mailed on Oct. 15, 2012 for U.S. Appl. No. 13/048,842, filed Mar. 15, 2011, nine pages.
Non-Final Office Action mailed on Oct. 10, 2012 for U.S. Appl. No. 13/048,844, filed Mar. 15, 2011, 11 pages.
Non-Final Office Action mailed on Oct. 4, 2012 for U.S. Appl. No. 13/091,116, filed Apr. 20, 2011, seven pages.
Non-Final Office Action mailed on Sep. 25, 2012, for U.S. Appl. No. 13/111,837, filed May 19, 2011, seven pages.
Non-Final Office Action mailed on Sep. 24, 2012 for U.S. Appl. No. 13/246,763, filed Sep. 27, 2011, 12 pages.
Non-Final Office Action mailed on Sep. 24, 2012 for U.S. Appl. No. 13/048,830, filed Mar. 15, 2011, seven pages.
Non-Final Office Action mailed on Sep. 21, 2012 for U.S. Appl. No. 13/535,070, filed Jun. 27, 2012, nine pages.
Non-Final Office Action mailed on Sep. 10, 2012 for U.S. Appl. No. 13/523,835, filed Jun. 14, 2012, eight pages.
Non-Final Office Action mailed on Sep. 7, 2012 for U.S. Appl. No. 13/048,837, filed Mar. 15, 2011, eight pages.
Notice of Allowance mailed on Nov. 9, 2012 for U.S. Appl. No. 13/019,273, filed Feb. 1, 2011, five pages.
Advisory Action dated Aug. 15, 2012 for U.S. Appl. No. 12/725,450.
Non-Final Office Action dated Sep. 7, 2012 for U.S. Appl. No. 13/048,837.
Non-Final Office Action dated Sep. 10, 2012 for U.S. Appl. No. 13/523,835.
Non-Final Office Action dated Sep. 21, 2012 for U.S. Appl. No. 13/535,070.
Non-Final Office Action dated Sep. 24, 2012 for U.S. Appl. No. 13/246,763.
Non-Final Office Action dated Sep. 24, 2012 for U.S. Appl. No. 13/048,830.
Non-Final Office Action dated Sep. 25, 2012 for U.S. Appl. No. 13/111,837.
Non-Final Office Action dated Oct. 4, 2012 for U.S. Appl. No. 13/091,116.
Non-Final Office Action dated Oct. 10, 2012 for U.S. Appl. No. 13/048,844.
Non-Final Office Action dated Oct. 15, 2012 for U.S. Appl. No. 13/048,842.
Final Office Action dated Oct. 16, 2012 for U.S. Appl. No. 13/246,775.
European Examination Report dated Oct. 22, 2012 for EP Appln. No. 10810835.8.
Extended European Search Report dated Oct. 22, 2012 for European Appln. No. 10823909.6.
Final Office Action dated Oct. 23, 2012 for U.S. Appl. No. 13/019,273.
Notice of Allowance dated Nov. 9, 2012 for U.S. Appl. No. 13/019,273.
Final Office Action dated Dec. 4, 2012 for U.S. Appl. No. 13/487,135.
Final Office Action dated Dec. 5, 2012 for U.S Appl. No. 12/966,943.
European Search Report & Search Opinion dated Dec. 7, 2012 for European Application No. 11758075.3.
Final Office Action dated Dec. 10, 2012 for U.S. Appl. No. 12/966,962.
Advisory Action dated Dec. 28, 2012 for U.S. Appl. No. 13/246,775.
Non-Final Office Action dated Jan. 2, 2013 for U.S. Appl. No. 13/545,944.
Final Office Action dated Jan. 15, 2013 for U.S. Appl. No. 13/487,121.
Final Office Action dated Jan. 17, 2013 for U.S. Appl. No. 13/487,118.
Final Office Action dated Jan. 29, 2013 for U.S. Appl. No. 13/048,837.
Final Office Action dated Jan. 31, 2013 for U.S. Appl. No. 13/535,070.
Final Office Action dated Feb. 1, 2013 for U.S. Appl. No. 13/523,835.
Final Office Action dated Feb. 15, 2013 for U.S. Appl. No. 13/048,830.
Advisory Action dated Feb. 25, 2013 for U.S. Appl. No. 13/487,135.
Final Office Action dated Feb. 25, 2013 for U.S. Appl. No. 13/048,842.
Final Office Action dated Mar. 14, 2013 for U.S. Appl. No. 13/091,116.
Advisory Action dated Apr. 11, 2013 for U.S. Appl. No. 13/048,837.
Non-Final Office Action dated Apr. 15, 2013 for U.S. Appl. No. 13/246,775.
Final Office Action dated Apr. 19, 2013 for U.S. Appl. No. 13/545,944.
Notice of Allowance dated Apr. 29, 2013 for U.S. Appl. No. 13/048,830.
Final Office Action dated Apr. 29, 2013 for U.S. Appl. No. 13/048,844.
Notice of Allowanced dated Apr. 30, 2013 for U.S. Appl. No. 13/048,842.
Notice of Allowance dated May 15, 2013 for U.S. Appl. No. 13/535,070.
Advisory Action dated Jun. 18, 2013 for U.S. Appl. No. 12/902,133.
Advisory Action dated Jun. 18, 2013 for U.S. Appl. No. 13/523,835.
Notice of Allowance dated Jun. 24, 2013 for U.S. Appl. No. 12/966,962.
M. William Apoutou N'dijin: "Transducteur torique a Ultrasons Focalises de Haute Intensite pour generer des ablations volumineuses", Dec. 17, 2008, XP055009820, URL: http://u556.lyon.inserm.fr/theses/pdf/ndjin.pdf.
Foreign Office Action dated Jun. 24, 2013 for EP Appln. No. 10823909.6.
European Examination Report dated Jun. 24, 2013 for EP Appln. No. 10810835.8.
Final Office Action dated Jul. 1, 2013 for U.S. Appl. No. 13/246,763.

* cited by examiner

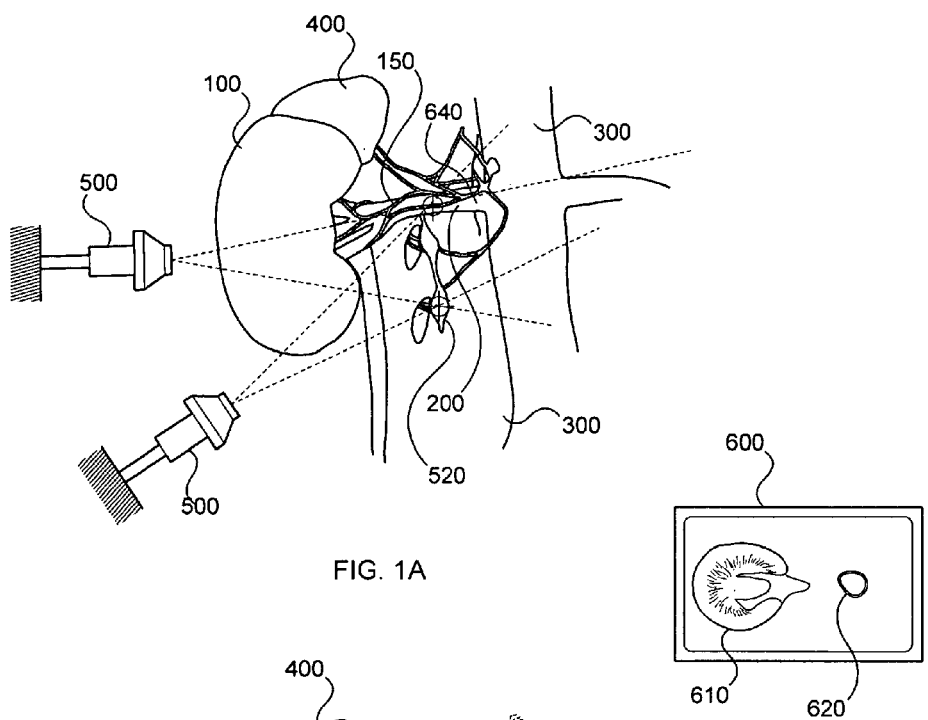
FIG. 1A
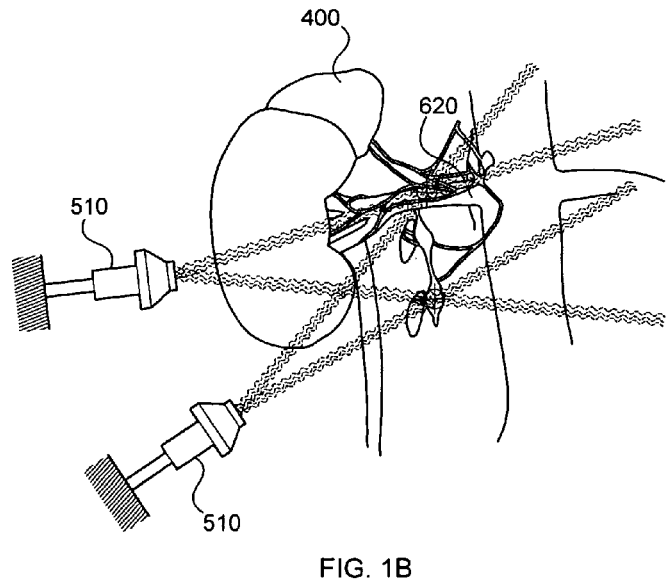
FIG. 1B
FIG. 1C

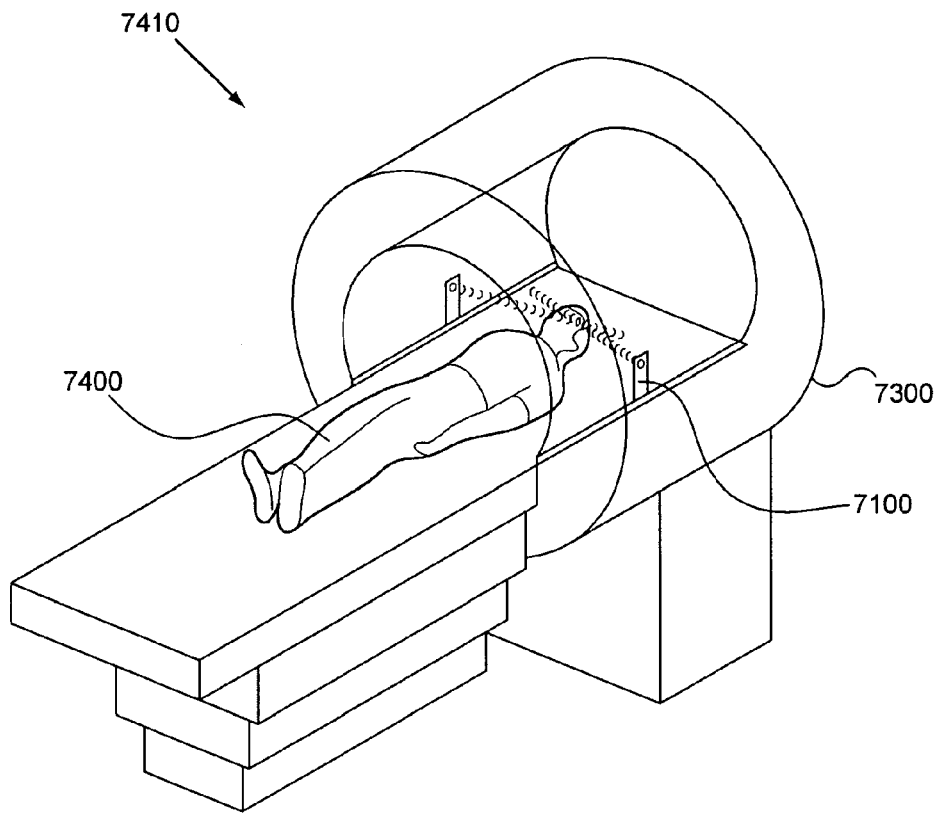
FIG. 11A
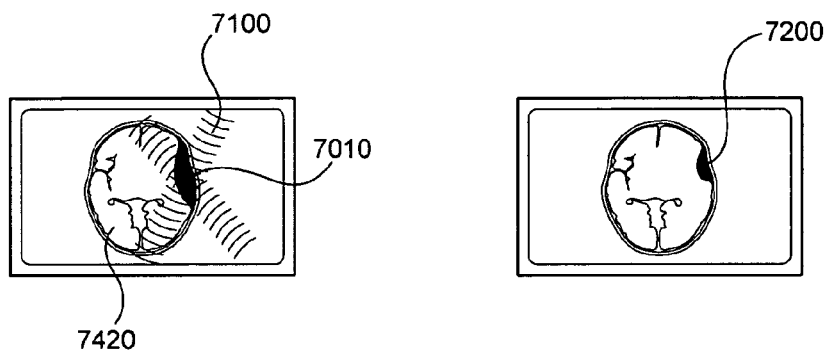
FIG. 11B
FIG. 11C

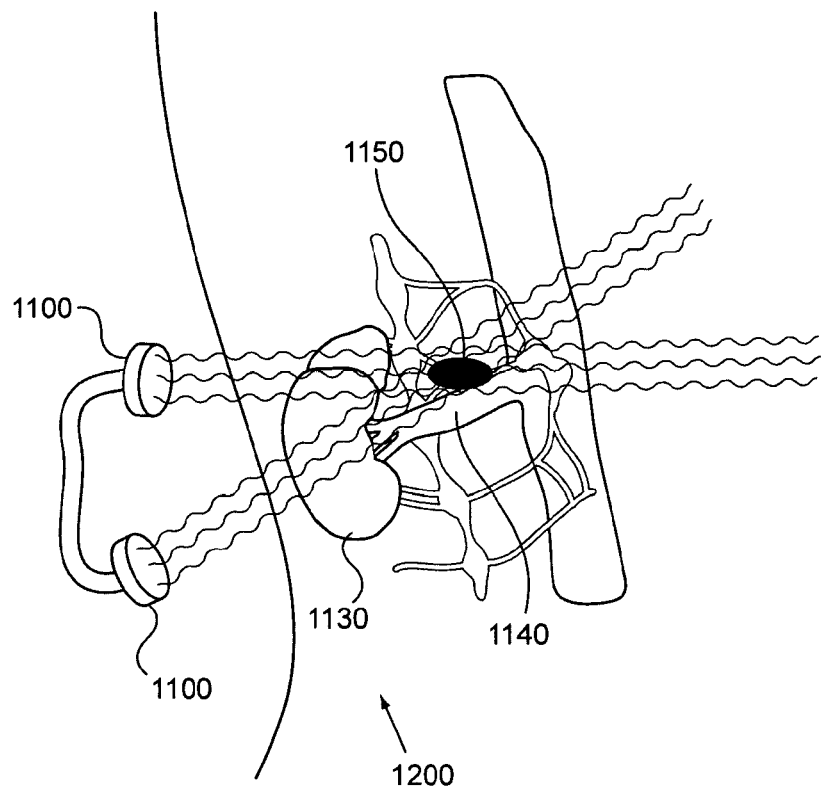
FIG. 17A
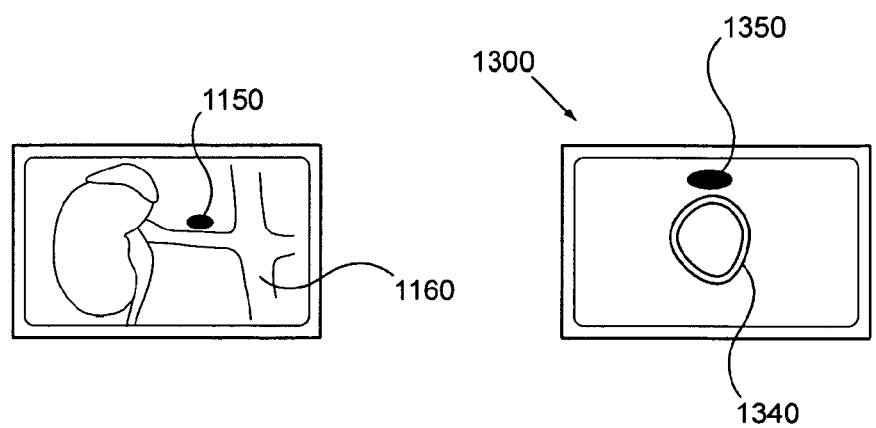
FIG. 17B
FIG. 17C

METHODS AND DEVICES TO MODULATE THE AUTONOMIC NERVOUS SYSTEM WITH ULTRASOUND

PRIORITY DATA

This application is a continuation of U.S. patent application Ser. No. 12/685,655 filed Jan. 11, 2010, pending, which claims priority to, and the benefit of U.S. Provisional Patent Application No. 61/256,983 filed Oct. 31, 2009, now lapsed, U.S. Provisional Patent Application No. 61/250,857 filed Oct. 12, 2009, now lapsed, U.S. Provisional Patent Application No. 61/261,741 filed Nov. 16, 2009, now lapsed, and U.S. Provisional Patent Application No. 61/291,359 filed Dec. 30, 2009, now lapsed, the entire disclosures of all of which are expressly incorporated by reference herein.

BACKGROUND

Energy delivery from a distance involves transmission of energy waves to affect a target some distance a way. It allows for more efficient delivery of energy to targets and greater cost efficiency and technologic flexibility on the generating side. For example, cellular phones receive targets from towers close to the user and the towers communicate with one another over a long range; this way, the cell phones can be low powered and communicate over a relatively small range yet the network can quickly communicate across the world. Similarly, electricity distribution from large generation stations to the users is more efficient than the users themselves looking for solutions.

In terms of treating a patient, delivering energy over a distance affords great advantages as far as targeting accuracy, technologic flexibility, and importantly, limited invasiveness into the patient. In a simple form, laparoscopic surgery has replaced much of the previous open surgical procedures and lead to creation of new procedures and devices as well as a more efficient procedural flow for disease treatment. Laparoscopic tools deliver the surgeon's energy to the tissues of the patient from a distance and results in improved imaging of the region being treated as well as the ability for many surgeons to visualize the region at the same time. Perhaps most important is the fact that patients have much less pain, fewer complications, and the overall costs of the procedures are lower.

Continued advances in computing, miniaturization and economization of energy delivery technologies, and improved imaging will lead to still greater opportunities to apply energy from a distance into the patient and treat disease.

SUMMARY OF INVENTION

What is described herein are procedures and devices which advance the art of medical procedures involving transmitted energy to treat disease. That is, the procedures and devices described below follow along the lines of: 1) transmitting energy to produce an effect in a patient from a distance; 2) allowing for improved imaging or targeting at the site of treatment; 3) creating efficiencies through utilization of larger and more powerful devices from a position of distance from the patient as opposed to attempting to be directly in contact with the target.

In some embodiments, an imaging system is provided, as is a therapeutic delivery system.

In some embodiments, regions of the eye other than the retina are targeted with ablative or sub-ablative energy from outside the eye.

In some embodiments, the ciliary muscles are targeted and in some embodiments, the zonules surrounding the lens are targeted. In certain embodiments related to the eye, presbyopia is treated and in certain embodiments, elevated intraocular pressure is treated.

In some embodiments, the macula is targeted with non-ablative focused energy. Non-ablative focused or unfocused energy can be utilized to assist in the transcleral or intravitreal release of bioactive agents into the eye.

In some embodiments, non-focal, non-ablative energy is applied to the sclera to assist in the transcleral migration of bioactive materials to the choroidal space below the retina.

In some embodiments, ducts such as the fallopian tubes or the vas deferens are targeted for permanent or semi-permanent sterilization using ablative energy.

In some embodiments, vascular structures such as the saphenous vein, femoral vein, and iliac veins are directly targeted to treat venous diseases such as occlusions or faulty venous valves.

In some embodiments, intra-vascular clots, devices, or other vascular abnormalities such as aneurysms or arterial-venous malformations, are targeted.

In some embodiments, sympathetic nerves surrounding arteries are targeted for ablation or sub-ablative interruption. In some embodiments, the renal nerves which surround the pedicles of the kidneys are targeted. In some embodiments, circles or elliptical rings are created around the renal arteries and in some embodiments, the circles or rings are created closer to the bifurcation of the renal arteries as they reach the kidneys. In other embodiments, nerves running down the aorta are targeted as they branch off to the renal arteries.

In some embodiments, whole or partial sympathetic ganglia positioned close to blood vessels are targeted. In some embodiments, ganglia along the sympathetic chain along the spine are targeted as entire structures to target and alter physiologic processes. In other embodiments, the dorsal roots of the spinal cord are targeted with energy to partially or fully ablate the renal afferent nerves traveling through them.

In some embodiments, nerves to joints are targeted with ablative or non-ablative energy such as for example, the spine, the knee, or the hip.

In some embodiments, vessels are detected and placed in a coordinate frame to be treated with the focused energy system but regions (for example, nerves) just outside the vessels are treated. For example, the carotid artery, superior mesenteric artery, aorta, vena cava, renal veins, iliac arteries, ophthalmic artery, and ciliary arteries are all arteries which are potential targets for interruption of surrounding nerves. The vessels, however, are the targets localized by the external imaging and energy delivery systems.

In some embodiments, a device and method to interrupt nerve fibers, at least partially, from a position external to a patient is described. The embodiment involves the application of energy from a region external to the patient to the region of the nerve fibers. In some embodiments, energy is delivered from multiple directions and meet at the region of the nerve so as to deliver the effect.

In some embodiments, an external energy source delivers energy from two difference positions to focus energy on a region of interest (for example, the sympathetic nerve regions of the renal arteries).

In another embodiment, image detectors are embedded in the devices delivering the energy so that the imaging of the region of interest is also determined from two different angles to determine the location of the target in three dimensions.

In another embodiment, range finders (e.g. acoustic or sonar) are used to detect distances or positions of structures.

In some embodiments, a renal artery is detected using doppler ultrasound technology. By detecting the position of the renal arteries from more than one angle via doppler triangulation, a three dimensional map can be created and the renal artery can be mapped into a coordinate reference frame. A pattern of energy can be applied to the renal artery based on the knowledge of the coordinate reference frame. Once the renal artery is placed in the coordinate frame, an algorithm is utilized to localize the delivery of focused ultrasound to heat the adventitia of the artery which contains the sympathetic nerves to the kidney and thereby decreasing the sympathetic stimulus to the kidney to potentially control hypertension.

In other embodiments, vessels are detected and placed in a coordinate frame to be treated with the focused energy system. For example, the carotid artery, superior mesenteric artery, aorta, vena cava, renal veins, iliac arteries, ophthalmic artery, and ciliary arteries are all arteries which are potential targets of sympathetic nerve interruption. In some embodiments, the techniques described can be applied to any other blood vessel adventitia or nerve plexus surrounding any blood vessel in the body.

In some embodiments, the location of the stomach is utilized because of its position overlying the celiac plexus and position partially overlying the abdominal aorta. In this embodiment, a nasogastric tube is placed inside the stomach and can be utilized to stimulate or inhibit the celiac axis through the stomach wall using focused or non-focused energy sources.

In some embodiments, the celiac axis or associated nerves can also be directly ablated using energy based transducers through the stomach or through the aorta or from an external position.

In another embodiment, ionizing radiation is used and generated from equipment such as a megavoltage linear accelerator, proton beam accelerator, or orthovoltage X-ray generator.

In some embodiments, CT scan imaging or other imaging systems (for example, ultrasound), such as MRI can be used to target the region around the renal arteries where the sympathetic nerves sit.

In some embodiments, the ionizing radiation sources may also be coupled to CT or MRI scanners which can further aid in the identification of the region of the sympathetic nerve plexus.

In some embodiments, the ultrasound transducers are placed externally and the renal arteries are located in more than one axis using a doppler signal detected from the renal artery blood flow.

In some embodiments, an arrangement of the ultrasound transducers is such that each transducer has the ability to be moved relative to one another and with respect to the target (e.g. renal blood vessels). Such movement allows for adjustment of focal distance and position in the X-Y plan which may change with position.

In some embodiments, a kidney and a renal artery, or just a kidney, is targeted with the ultrasound transducers.

In some embodiments, ultrasound transducers are used to detect Doppler blood flow and simulate the position of the heating spot at the focal region of the transducers.

In some embodiments, a three dimensional view of the renal arteries and renal pedicle is obtained using the ultrasonic images so that the heated region is simulated in three dimensions so as to avoid the critical structures around the renal pedicle such as the renal vein, adrenal artery, and the adrenal gland itself.

In some embodiments, a three-dimensional image of a renal artery enables precise placement of the heat generating spot because there are nerves proximal to the generated spot. In some embodiments, coupling of the renal artery doppler signal using two separate detectors allows the three dimensional coordinates of the renal artery to be determined in real space. In some embodiments, once the renal artery position is determined in real space, the 3D location of the heating via the therapeutic ultrasound transducers can be determined, in theory, quite quickly. Heating damage to organs surrounding the renal arteries can also be determined, modeled, and minimized.

In some embodiments, a puncture in the skin may be needed so as to take advantage of additional refinements in technology or to treat patients (e.g. obese patients) who are not amenable to completely external therapy. In this embodiment, the puncture in the skin may enable a catheter to be passed into an artery or vein and to the renal artery or vein. In some embodiments, a catheter is placed percutaneously, directly to the nerve region surrounding the vessels; that is, not transvascularly.

In other embodiments, catheters may be placed through the subcutaneous tissues and into the space around the renal artery or vein. In either of these embodiments, the sympathetic nerves can be ablated or the nerve conduction pathways can otherwise be interrupted to result in a decrease in neurotransmitter release from the sympathetic terminals at the level of the kidney.

In addition to, or in place of, the renal sympathetic nerves, in some embodiments, it may be desirable to ablate or partially inhibit nerves which relate to the carotid or aortic baroreceptors. For example, cardiac afferent nerves have been known to dampen the carotid body response when activated which results in a loss of the parasympathetic response to elevated blood pressure. In such a scenario, the cardiac afferent nerves can be ablated so that the baroreceptor response remains sensitive to increased blood pressure and can stimulate the parasympathetic system to decrease adrenergic drive in the face of elevated blood pressure.

In some embodiments, the sympathetic or parasympathetic nerves leading to the eye are ablated, stimulated, partially ablated, or partially stimulated so as to control intraocular hypertension or other physiologic processes. These sympathetic nerves are well known as being causative for increases in intraocular pressure. Indeed, a best selling pharmaceutical, tenoptic, acts against the adrenergic response in the eye and so ablating the sympathetic nerves would offer a more permanent fix to the elevated intraocular blood pressure.

In one embodiment, the ultrasound transducers used for ablation also contain at least one imaging transducer. The imaging transducer can be utilized for quick imaging and registration with the MRI or the transducer can be utilized for detection of fiducials within the treatment region. Such fiducials can be placed in the field or may be naturally present. In one embodiment, an intravascular catheter is placed with a recognizeable beacon to indicate the position of the catheter, artery, and hence the nerves surrounding the artery.

In another embodiment, radiation is applied to the region outside the artery to prevent re-growth of the sympathetic nerves after ablation.

In another embodiment, ablative energy is applied to a region of a fallopian tube to close the tube and prevent ovulation and transfer of ovum to a uterus.

In one embodiment, a method of inhibiting the function of a nerve traveling with an artery comprises; providing an external imaging modality to determine the location of the artery through the skin of a patient; placing the artery in a three dimensional coordinate reference based on the imaging; placing a therapeutic energy generation source in a three dimensional coordinate reference frame; coupling the three dimensional coordinate frame of the energy source and the artery; modeling the delivery of energy to the adventitial region of the artery or a region adjacent to the artery where a nerve travels; delivering therapeutic energy from the therapeutic energy source, from at least two different angles, through the skin of a patient, to intersect at an artery or the region adjacent to the artery to at least partially inhibit the function of a nerve.

In some embodiments, the imaging source is one of: ultrasound, MRI, and CT.

In some embodiments, the therapeutic energy is ultrasound.

In some embodiments, the artery is a renal artery.

In some embodiments the involve placing the artery in a three dimensional reference frame involving locating the artery using a doppler ultrasound signal.

In some embodiments, the fiducial is placed internal to the patient.

In some embodiments, the fiducial is temporarily placed in a position internal to the patient.

In some embodiments the fiducial is a catheter placed in the artery of the patient.

In some embodiments the catheter is detectable using an acoustic signal and said imaging modality is ultrasound.

In some embodiments, the method involves therapeutic energy from the energy source which is delivered in a distribution along the length of the artery.

In some embodiments the therapeutic energy is ionizing radiation.

In some embodiments, a system to inhibit the function of a nerve traveling with a renal artery comprises a detector to determine the location of the renal artery and renal nerve through the skin of a patient; an ultrasound component to deliver therapeutic energy through the skin from at least two directions to the nerve surrounding the renal artery; a modeling algorithm comprising an input and an output said input to the modeling algorithm comprising a three dimensional coordinate space containing a therapeutic energy source and the position of the renal artery; and, the output from the modeling algorithm comprises: the direction and energy level of the ultrasound component; a locateable fiducial, adapted to be temporarily placed in the artery of a patient and communicate with the detector to determine the location of the renal artery in a three dimensional reference, the information regarding the location transmittable as the input to the model.

In some embodiments, the fiducial is a passive reflector of ultrasound.

In some embodiments, the system fiducial generates radiofrequency energy.

In some embodiments, the system fiducial is activated to transmit energy based on a signal from an ultrasound generator.

In some embodiments, the system output from the model instructs the ultrasound component to deliver a lesion on the artery in which the major axis of the lesion is longitudinal along the length of the artery.

In some embodiments, the system output from the model instructs the ultrasound component to deliver multiple lesions around an artery simultaneously.

In some embodiments, the system output from the model instructs the ultrasound component to deliver a circumferential lesion around the artery.

In some embodiments, a lesion is placed around the renal artery just proximal to the bifurcation of the artery in the hilum of the kidney.

DESCRIPTION OF FIGURES

FIGS. 1a-c depict the focusing of energy sources on nerves of the autonomic nervous system.

FIG. 11 depicts treatment of brain lesions using cross sectional imaging.

FIG. 17a depicts the application of multiple transducers to treat regions of the autonomic nervous system.

FIGS. 17b-f depict methods and devices to treat a specific region surrounding an artery.

DETAILED DESCRIPTION OF THE INVENTION

Figure 2:
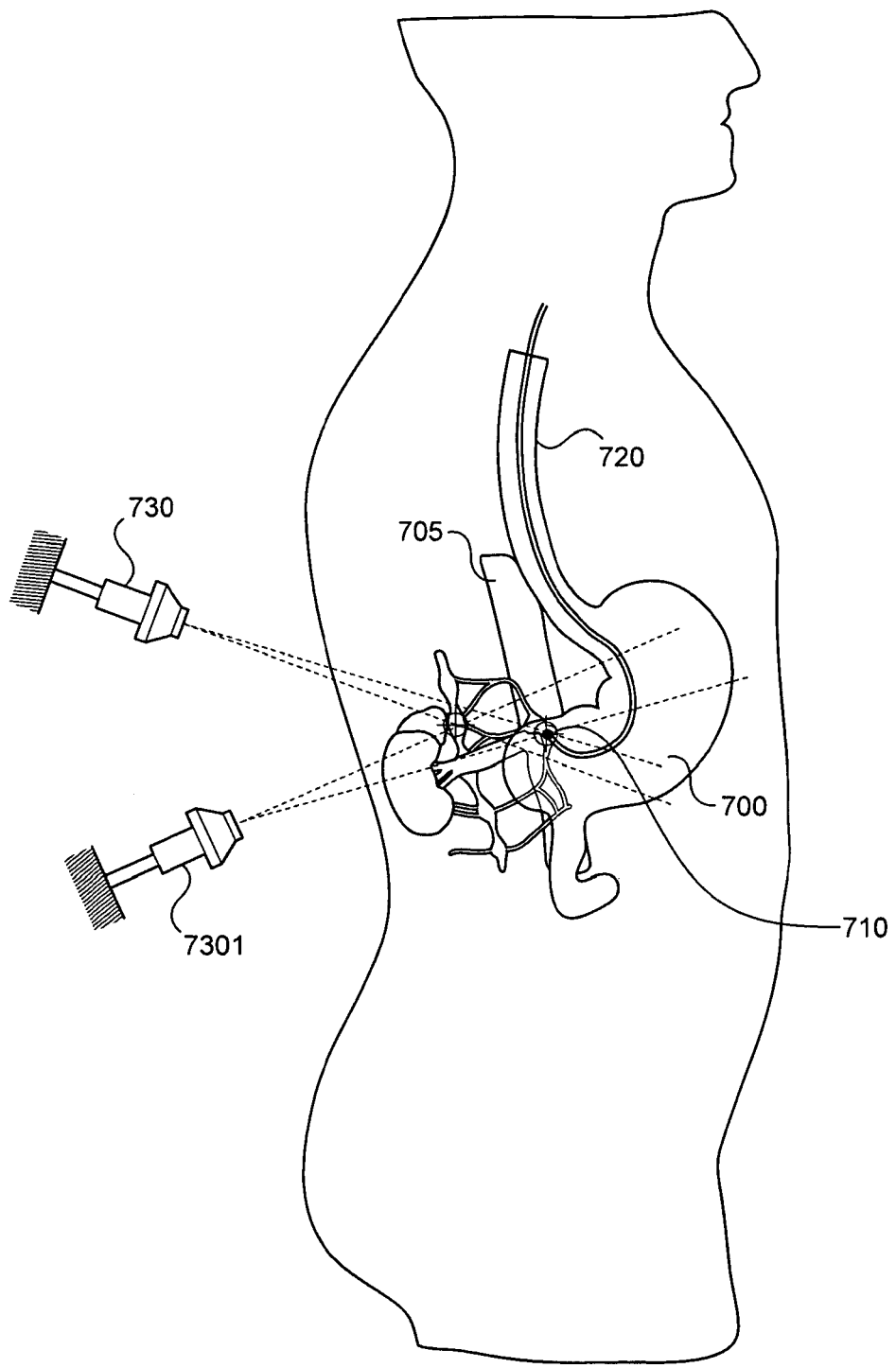
FIG. 2 depicts targeting and/or therapeutic ultrasound delivered through the stomach to the autonomic nervous system posterior to the stomach.

Congestive Heart Failure ("CHF") is a condition which occurs when the heart becomes damaged and blood flow is reduced to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. For example, as the heart struggles to pump blood, the cardiac output is maintained or decreased and the kidneys conserve fluid and electrolytes to maintain the stroke volume of the heart. The resulting increase in pressure further overloads the cardiac muscle such that the cardiac muscle has to work harder to pump against a higher pressure. The already damaged cardiac muscle is then further stressed and damaged by the increased pressure. Moreover, the fluid overload and associated clinical symptoms resulting from these physiologic changes result in additional hospital admissions, poor quality of life, and additional costs to the health care system. In addition to exacerbating heart failure, kidney failure can lead to a downward spiral and further worsening kidney function. For example, in the forward flow heart failure described above, (systolic heart failure) the kidney becomes ischemic. In backward heart failure (diastolic heart failure), the kidneys become congested vis-à-vis renal vein hypertension. Therefore, the kidney can contribute to its own worsening failure.

The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys. The resulting hypertension also has dramatic influence on the progression of cerebrovascular disease and stroke.

The autonomic nervous system is a network of nerves which affect almost every organ and physiologic system to a variable degree. Generally, the system is composed of sympathetic and parasympathetic nerves. For example, the sympathetic nerves to the kidney traverse the sympathetic chain along the spine and synapse in the celiac ganglia, then proceeding to innervate the kidney with the post-ganglionic fibers. Within the renal nerves, which travel along the renal hila, are the post-ganglionic sympathetic nerves and the afferent nerves from the kidney. The afferent nerves deliver information from the kidneys back to the sympathetic nervous system and their ablation is at least partially responsible for the improvement seen in blood pressure after renal nerve ablation. It has also been suggested and partially proven experimentally that the baroreceptor response at the level of the carotid sinus is mediated by the renal artery afferent nerves such that loss of the renal artery afferent nerve response blunts the response of the carotid baroreceptors to changes in arterial blood pressure It has been established in animal models that the heart failure condition results in abnormally high sympathetic activation of the kidneys. An increase in renal sympathetic nerve activity leads to increased removal of water and sodium from the body, as well as increased renin secretion which stimulates aldosterone secretion from the adrenal gland. Increased renin secretion can lead to vasoconstriction of blood vessels supplying the kidneys, which leads to a decrease in renal blood flow. Reduction in sympathetic renal nerve activity, e.g., via de-innervation, may reverse these processes.

Recent clinical work has shown that de-innervation of the renal sympathetic chain nerves can lead to long term reduction of the need for blood pressure medications and improvement in blood pressure (O'Brien Lancet 2009 373; 9681 incorporated by reference). The device used in this trial utilized highly localized radiofrequency (RF) ablation to ablate the renal artery adventitia with the presumption that the nerves surrounding the renal artery are being treated as well. The procedure is performed in essentially a blind fashion in that the exact location of the sympathetic nerves is not known prior to, during, or after the procedure. In addition, the wall of the renal artery is invariably damaged by the RF probe and patients whose vessels have a great deal of atherosclerosis cannot be treated safely. In addition, depending on the distance of the nerves from the vessel wall, the energy may not consistently lead to ablation or interruption. Finally, the use of internal catheters may not allow for treatment inside the kidney or inside the aorta if more selective or less selective blockade of the renal sympathetic nerves is desired.

Ultrasound is a cyclically generated sound pressure wave with a frequency greater than the upper limit of human hearing . . . 20 kilohertz (kHz). In medicine, ultrasound is widely utilized because of its ability to penetrate tissues. Reflection of the sound waves reveals a signature of the underlying tissues and as such, ultrasound can be used extensively for diagnostics and potentially therapeutics as well in the medical field. As a therapy, ultrasound has the ability to both penetrate tissues and can be focused to create ablation zones. Because of its simultaneous ability to image, ultrasound can be utilized for precise targeting of lesions inside the body.

Ultrasound can be utilized for its forward propagating waves and resulting reflected waves or where energy deposition in the tissue and either heating or slight disruption of the tissues is desired. For example, rather than relying on reflections for imaging, lower frequency ultrasonic beams (e.g. <1 MHz) can be focused at a depth within tissue, creating a heating zone or a defined region of cavitation in which microbubbles are created, cell membranes are opened to admit bioactive molecules, or damage is otherwise created in the tissue. These features of ultrasound generally utilize frequencies in the 0.25 Megahertz (MHz) to 10 MHz range. Focusing is or may be required so that the surface of the tissue is not excessively injured or heated by single beams.

SONAR is an acronym for sound navigation and ranging and is a method of acoustic localization. Sound waves are transmitted through a medium and the time for the sound to reflect back to the transmitter is indicative of the position of the object of interest. Doppler signals are generated by a moving object. The change in the forward and reflected wave results in a velocity for the object.

Cross-sectional imaging is utilized to visualize the internal anatomy of patients via radiation (CT) or magnetic fields (MRI). Ultrasound can also be utilized to obtain cross-sections of specific regions but only at high frequencies; therefore, ultrasound is typically limited to imaging superficial body regions. CT and MRI are often more amenable to cross sectional imaging because the radiations penetrate well into tissues. In addition, the scale of the body regions is maintained such that the anatomy within the coordinate references remains intact relative to one another; that is, distances between structures can be measured. With ultrasound, scaling can be more difficult because of unequal penetration as the waves propagate deeper through the tissue. CT scans and MRIs and even ultrasound devices can be utilized to create three dimensional representations and reconstructed cross-sectional images of patients; anatomy can be placed in a coordinate reference frame using a three dimensional representation. Once in the reference frame, energy devices (transducers) can be placed in positions and energy emitting devices directed such that specific regions of the body are targeted. Once knowledge of the transducer position is known relative to the position of the target in the patient body, energy can be delivered to the target.

In one embodiment, ultrasound is focused on the region of the renal arteries from outside the patient; the ultrasound is delivered from multiple angles to the target allowing the current invention to overcome many of the deficiencies in previous methods and devices put forward to ablate renal sympathetic nerves which surround the renal arteries.

Specifically, one embodiment of this invention allows for precise visualization of the ablation zone so that the operator can be confident that the correct region is ablated and that the incorrect region is not ablated. Because some embodiments do not require a puncture in the skin, they are considerably less invasive, which is more palatable and safer from the patient standpoint. Moreover, unusual anatomies and atherosclerotic vessels can be treated using external energy triangulated on the renal arteries to affect the sympathetic and afferent nerves to and from the kidney respectively.

With reference to FIG. 1a, the human renal anatomy includes the kidneys 100 which are supplied with oxygenated blood by the renal arteries 200 and are connected to the heart via the abdominal aorta 300. Deoxygenated blood flows from the kidneys to the heart via the renal veins (not shown) and thence the inferior vena cava (not shown). The renal anatomy includes the cortex, the medulla, and the hilum. Blood is delivered to the cortex where it filters through the glomeruli and is then delivered to the medulla where it is further filtered through a series of reabsorption and filtration steps in the loops of henle and individual nephrons. The hila are the regions where the major vessels and nerves travel to and from the kidneys.

Energy transducers 500 (FIG. 1a) deliver energy transcutaneously to the region of the sympathetic ganglia 520 or the post-ganglionic renal nerves 150 or the nerves leading to the adrenal gland 400. The energy is generated from outside the patient, from multiple directions, and through the skin to the region of the renal nerves which surround the renal artery 640. The energy can be focused or non-focused but in one preferred embodiment, the energy is focused with high intensity focused ultrasound (HIFU). Focusing occurs by delivering energy from at least two different angles through the skin to meet at a focal point where the highest energy intensity occurs. At this spot, a therapy is delivered and the therapy can be sub-threshold nerve interruption, ablation (complete interruption) of the nerves, or targeted drug delivery. To ablate the nerves, temperatures greater than 40 degrees should be generated for a time period greater than several minutes. If the temperature is increased beyond 50-60 degrees, the time required for heating is decreased considerably. In some embodiments, an imaging modality is included as well in the system.

The delivered energy can be ionizing or non-ionizing energy. Forms of non-ionizing energy can include electromagnetic energy, radiofrequency energy, and light based energy. Forms of ionizing energy include x-ray, proton beam, gamma rays, electron beams, and alpha rays. In some embodiments, the energy modalities are combined. For example, heat ablation of the nerves is performed and then ionizing radiation is delivered to the region to prevent re-growth of the nerves.

Alternatively, ionizing radiation is applied first as an ablation modality and then heat applied afterward in the case of re-growth of the tissue as re-radiation may not be possible. Ionizing radiation may prevent or inhibit the re-growth of the nervous tissue around the vessel if there is indeed re-growth of the nervous tissue.

In some embodiments, external neuromodulation is performed in which low energy ultrasound is applied to the nerve region to modulate the nerves. For example, it has been shown in the past that low intensity (e.g. non-thermal) ultrasound can affect nerves at powers which range from 30-500 mW/Cm$^2$ whereas HIFU (thermal modulation), by definition generates heat at a focus, requires power levels exceeding 1000 W/Cm$^2$. The actual power flux to the region to be ablated is dependent on the environment including surrounding blood flow and other structures. With low intensity ultrasound, the energy does not have to be so strictly focused to the target because it's a non-ablative energy; that is, the vibration or mechanical pressure may be the effector energy and the target may have a different threshold for effect depending on the tissue. However, even low energy ultrasound may require focusing if excessive heat to the skin is a worry or if there are other susceptible structures in the path and only a pinpoint region of therapy is desired.

In FIG. 1a, and in one embodiment, a renal artery is detected 640 with the assistance of imaging techniques 600 such as Doppler ultrasound, MRI, or a CT scan. With an image of the region to be treated, measurements in multiple directions on a series of slices can be performed so as to create a three-dimensional representation of the area of interest. By detecting the position of the renal arteries from more than one angle via Doppler triangulation (for example) or another triangulation technique, a three dimensional positional map can be created and the renal artery can be mapped into a coordinate reference frame. In this respect, given that the renal nerves surround the renal blood vessels in the hilum, locating the direction and lengths of the blood vessels in three dimensional coordinate reference is the predominant component of the procedure to target the sympathetic nerves. Within the three dimensional reference frame, a pattern of energy can be applied to the vicinity of the renal artery from a device well outside the vicinity (and outside of the patient altogether) based on knowledge of the coordinate reference frame.

For example, once the renal artery is placed in the coordinate reference frame with the origin of the energy delivery device, an algorithm is utilized to localize the delivery of focused ultrasound to heat or apply mechanical energy to the adventitia and surrounding regions of the artery which contain sympathetic nerves to the kidney and afferent nerves from the kidney, thereby decreasing the sympathetic stimulus to the kidney and its afferent signaling back to the autonomic nervous system; affecting these targets will modulate the propensity toward hypertension which would otherwise occur. The ultrasonic energy delivery can be modeled mathematically by predicting the wave dissipation using the distances and measurements taken with the imaging modalities of the tissues and path lengths.

Imaging 600 of the sympathetic nerves or the sympathetic region (the target) is also utilized so as to assess the direction and orientation of the transducers relative to the target 620. Continuous feedback of the position of the transducers 500 relative to the target 150 is provided by the imaging system in which the coordinate space of the imaging system. The imaging may be a cross-sectional imaging technology such as CT or MRI or it may be an ultrasound imaging technology which yields faster real time imaging. In some embodiments, the imaging may be a combination of technologies such as the fusion of MRI/CT and ultrasound.

In the example of fusion, cross-sectional imaging (e.g. MRI/CT) is utilized to place the body of the patient in a three dimensional coordinate frame and then ultrasound is linked to the three dimensional reference frame and utilized to track the patient's body in real time under the ultrasound linked to the cross-sectional imaging. The lack of resolution provided by the ultrasound is made up for by the cross-sectional imaging since only a few consistent anatomic landmarks are required for an ultrasound image to be linked to the MRI image. As the body moves under the ultrasound, the progressively new ultrasound images are linked to the MRI images and therefore MRI "movement" can be seen at a frequency not otherwise available to an MRI series.

Figure 3A:
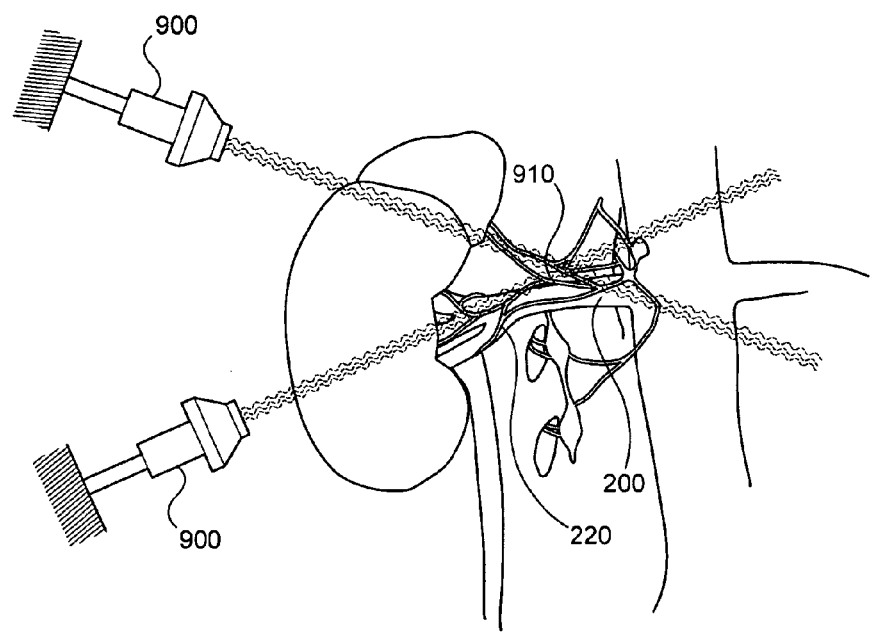
FIG. 3 depicts focusing of energy waves on the renal nerves
Figure 3B:
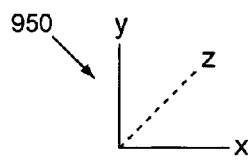

In one embodiment, ultrasound is the energy used to inhibit nerve conduction in the sympathetic nerves. In one embodiment, focused ultrasound (HIFU) is the energy used to inhibit sympathetic stimulation of the kidney by delivering waves from a position external to the body of a patient and focusing the waves on the sympathetic nerves on the inside of the patient and which surround the renal artery of the patient. As is depicted in FIG. 3, transducers 900 can emit ultrasound energy to the region of the renal sympathetic nerves at the renal pedicle. As shown in FIG. 1a, an image of the renal artery 620 using an ultrasound, MRI, or CT scan can be utilized to determine the position of the kidney 610 and the renal artery 620. Doppler ultrasound can be used to determine the location and direction of a Doppler signal from an artery and therefore enable the arteries and hence the sympathetic nerves around the artery to be much more visible so as to process the images and then utilize focused external energy to pinpoint the location and therapy of the sympathetic nerves. FIG. 1a also depicts the delivery of focused energy to the sympathetic nerve trunks which run along the vertebral column; the renal artery efferent nerves travel in these trunks. In another embodiment, ablation of the dorsal roots at the level of the ganglia or dorsal root nerves at T9-T11 (through which the afferent renal nerves travel) would produce the same or similar effect to ablation at the level of the renal arteries.

FIG. 1b illustrates the application of ionizing energy to the region of the sympathetic nerves on the renal arteries 620 or renal veins. In general, energy levels of greater than 20 Gy (Grey) are required for linear accelerators or low energy x-ray machines to ablate nervous tissue using ionizing energy; however, lower energy are required to stun, inhibit nervous tissue, or prevent regrowth of nervous tissue; in some embodiment, energy levels as low as 2-5 Gy or 5-10 Gy or 10 10-15 Gy are delivered in a single or fractionated doses.

Combinations of ionizing energy and other forms of energy can be utilized in this embodiment as well so as to prevent re-growth of the nervous tissue.

FIG. 2 illustrates the renal anatomy and surrounding anatomy with greater detail in that organs such as the stomach are shown in its anatomic position overlying the abdominal aorta and renal arteries. In this embodiment, energy is delivered through the stomach to reach an area behind the stomach. In this embodiment, the stomach is utilized as a conduit to access the celiac ganglion, a region which would otherwise be difficult to reach. The aorta 705 is shown underneath the stomach and the celiac ganglion 710 is depicted surrounding the superior mesenteric artery and aorta. A transorally placed tube 720 is placed through the esophagus and into the stomach. The tube overlies the celiac ganglion when placed in the stomach and can therefore be used to deliver sympatholytic devices or pharmaceuticals which inhibit or stimulate the autonomic celiac ganglia behind the stomach; these therapies would be delivered via transabdominal ultrasound or fluoroscopic guidance (for imaging) through the stomach. Similar therapies can be delivered to the inferior mesenteric ganglion, renal nerves, or sympathetic nerves traveling along the aorta through the stomach or other portion of the gastrointestinal tract. The Energy delivery transducers 730, 731 are depicted external to the patient and can be utilized to augment the therapy being delivered through the stomach to the celiac ganglion.

Temporary neurostimulators can also be placed through the tube, such as, for example, in an ICU setting where temporary blockage of the autonomic ganglia may be required. Temporary neurostimulators can be used to over pace the celiac ganglion nerve fibers and inhibit their function as a nerve synapse. Inhibition of the celiac ganglion may achieve a similar function as ablation or modulation of the sympathetic nerves around the renal arteries. That is, the decrease in the sympathetic activity to the kidneys (now obtained with a more proximal inhibition) leads to the lowering of blood pressure in the patient by decreasing the degree of sympathetic outflow from the sympathetic nerve terminals. In the celiac ganglia, the blood pressure lowering effect is more profound given that the celiac ganglia are pre-ganglionic and have more nerve fibers to a greater number of regions than each renal nerve.

FIG. 3 illustrates the renal anatomy more specifically in that the renal nerves 910 extending longitudinally along the renal artery, are located generally within, or just outside the adventitia, of the outer portion of the artery. Arteries are typically composed of three layers: the first is the intimal, the second is the media, and the third is the adventitia. The outer layer, the adventitia, is a fibrous tissue which contains blood vessels and nerves. The renal nerves are generally postganglionic sympathetic nerves although there are some ganglia which exist distal to the takeoff from the aorta such that some of the nerve fibers along the renal artery are in fact pre-ganglionic. By the time the fibers reach the kidney, the majority of the fibers are post-ganglionic.

Energy generators 900 deliver energy to the renal nerves accompanying the renal artery, depositing energy from multiple directions to target inhibition of the renal nerve complex. The energy generators can deliver ultrasound energy, ionizing radiation, light (photon) therapy, or microwave energy to the region. The energy can be non-focused in the case where a pharmaceutical agent is targeted to the region to be ablated or modulated. Preferably, however, the energy is focused, being applied from multiple angles from outside the body of the patient to reach the region of interest (e.g. sympathetic nerves surrounding blood vessels). The energy transducers 900 are placed in an X-Y-Z coordinate reference frame 950, as are the organs such as the kidneys. Once in the coordinate reference frame, cross-sectional imaging using MRI, CT scan, and/or ultrasound is utilized to couple the internal anatomy to the energy transducers. The transducers 900 in this embodiment are focused on the region of the renal nerves at the level of the renal blood vessels, the arteries and veins.

When applying ultrasonic energy across the skin to the renal artery region, energy densities of potentially over 1 $MW/cm^2$ might be required so as to reach the region of interest. The energy may be pulsed across the skin but for application of heat, the transducers must be focused; otherwise the skin and underlying tissues will receive too much heat. Under imaging with MRI, temperature can be measured with the MRI image. When low energy ultrasound is applied to the region, energy densities in the range of 50 $mW/cm^2$ to 500 mW/cm² may be applied. Low energy ultrasound may be enough to stun or partially inhibit the renal nerves. High intensity ultrasound applied to the region with only a few degrees of temperature rise may have the same effect. In some of the embodiments, cooling may be applied to the skin if the temperature rise is deemed too large to be acceptable. Alternatively, the ultrasound transducers can be pulsed or can be alternated with another set of transducers to effectively spread the heat across the surface of the skin.

In one method of altering the physiologic process of renal sympathetic excitation, the region around the renal arteries is imaged using CT scan, MRI, thermography, infrared imaging, pet imaging, SPECT imaging, or ultrasound, and the images are placed into a three dimensional coordinate reference frame. Energy transducers which can deliver ultrasound, light, radiation, ionizing radiation, or microwave energy are placed in the same three-dimensional reference frame as the renal arteries at which time an algorithm can determine how to direct the transducers to deliver energy to the region of the nerves. The algorithm consists of a targeting feature (planning feature) which allows for prediction of the position and energy deposition of the energy leaving the transducer. Once the three dimensional coordinate reference frames are linked or coupled, the planning and prediction algorithm can be used to precisely position the energy beams at a target in the body.

The original imaging utilized to locate the renal sympathetic region can be used to track the motion of the region during treatment. For example, the imaging technology used at time zero is taken as the baseline scan and subsequent scans at time t1 are compared to the baseline scan. The frequency of updates can range from a single scan every few seconds to many scans per second. With ultrasound as the imaging technology, the location might be updated at a rate greater than 50 Hz and up to several hundred Hz. With MRI as the imaging modality, the imaging refresh rate might be closer to 30 Hz. In other embodiments, internally placed fiducials transmit positional information at a high frequency and this information is utilized to fuse the target with an initial external imaging apparatus.

A test dose of energy can be applied to the renal sympathetic region and then a test performed to determine if there was an effect. For example, a small amount of heat can be delivered to the region of the sympathetic nerves and then a test of sympathetic activity such as microneurometry (detection of sympathetic nerve activity around muscles which correlates with heartbeats) can be performed. Past research has shown that the sympathetic nerves to the peripheral muscles are affected by interruption of the renal afferent nerves. The temperature rise with the small degree of heat can be determined through the use of MRI thermometry and the temperature rise can be determined or limited to an amount which is reversible.

Alternatively, ultrasonic imaging can be utilized to determine the approximate temperature rise of the tissue region. The speed of ultrasonic waves is dependent on temperature and therefore the relative speed of the ultrasound transmission from a region being heated will depend on the temperature, therefore providing measurable variables to monitor. In some embodiments, microbubbles are utilized to determine the rise in temperature. Microbubbles expand and then degrade when exposed to increasing temperature so that they can then predict the temperature of the region being heated. A technique called ultrasound elastography an also be utilized. In this embodiment, tissue elastography is dependent on temperature so the elastography may be utilized to track creatures.

In another embodiment, a test may be performed on the baroreceptor complex at the region of the carotid artery bifurcation. After the test dose of energy is applied to the renal artery complex, pressure can be applied to the carotid artery complex; typically, with an intact baroreceptor complex, the systemic blood pressure would decrease after application of pressure to the carotid artery.

Figure 4:
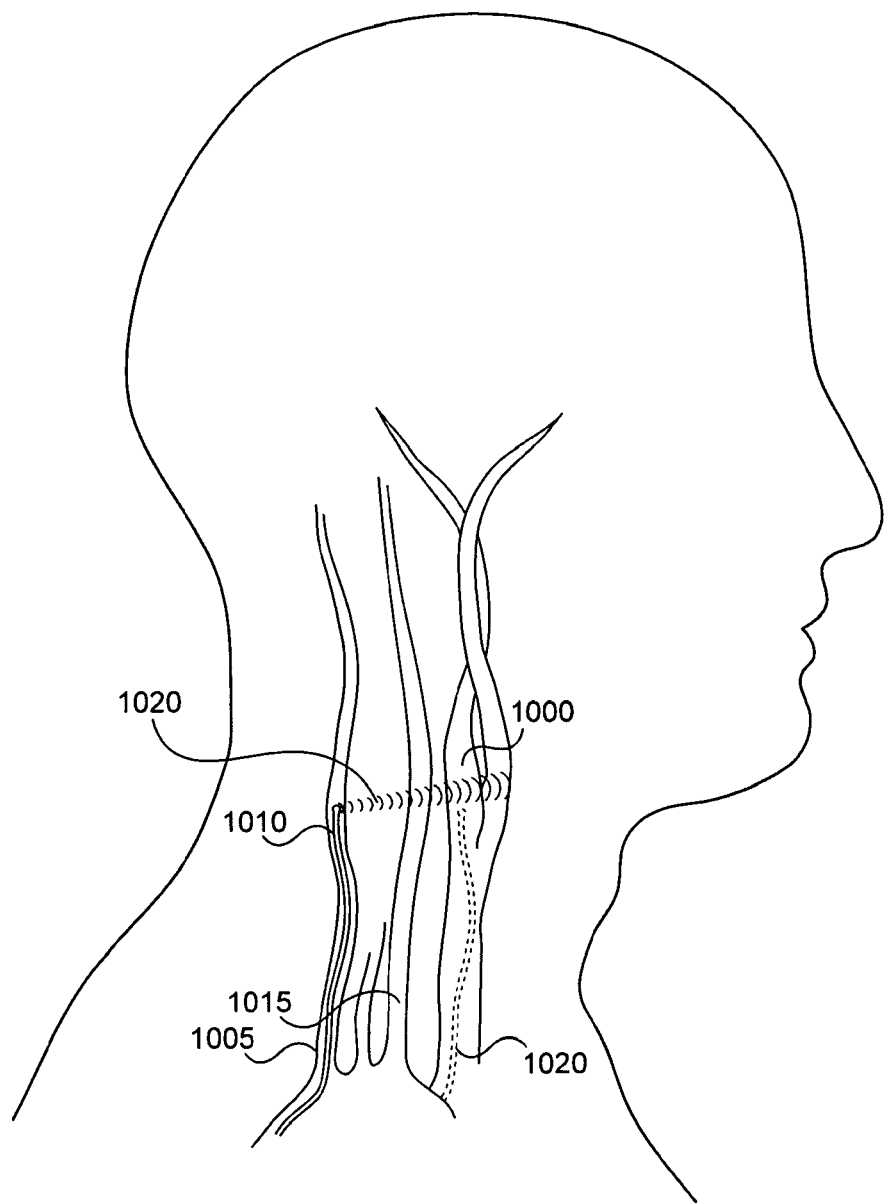
FIG. 4 depicts the application of energy to the autonomic nervous system surrounding the carotid arteries

Other regions of the autonomic nervous system can also be affected directly by the technology in this invention by applying energy from one region to another. For example, FIG. 4 illustrates a system in which external energy 1020 is applied to a portion of the autonomic nervous system, the carotid body complex 1000, through the internal jugular vein 1005, and to the carotid body 1000 and/or vagus nerve 1020 region. Ablative energy or electrical stimulation energy can be utilized to affect the transmission of signals to and from these nerves. The transmission in this complex can be augmented, interrupted, inhibited with over-stimulation, or a combination of these effects via energy (e.g. ultrasound, electrical stimulation, etc.)

A catheter 1010 is advanced into the internal jugular vein 1005 and when in position, stimulation or ablative energy is directed toward the autonomic nerves, the vagus nerve, and the carotid sinus from the catheter position in the venous system.

This therapy can be delivered on an acute basis such as for example in an ICU or critical care setting. In such a case, the therapy would be acute and intermittent, with the source outside the patient and the catheter within the patient as shown in FIG. 4. The therapy can be utilized during times of stress for the patient such that the sympathetic system is slowed down. After the intensive care admission is nearing a close, the catheter and unit can be removed from the patient.

Figure 5A:
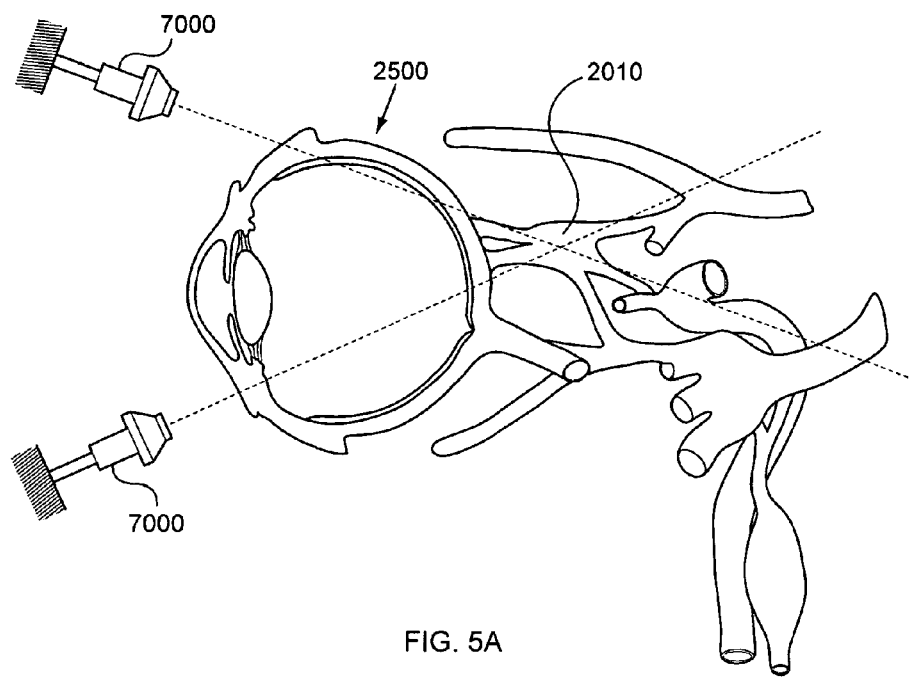
FIGS. 5a-b depict the application of focused energy to the autonomic nervous system of the eye.
Figure 5B:
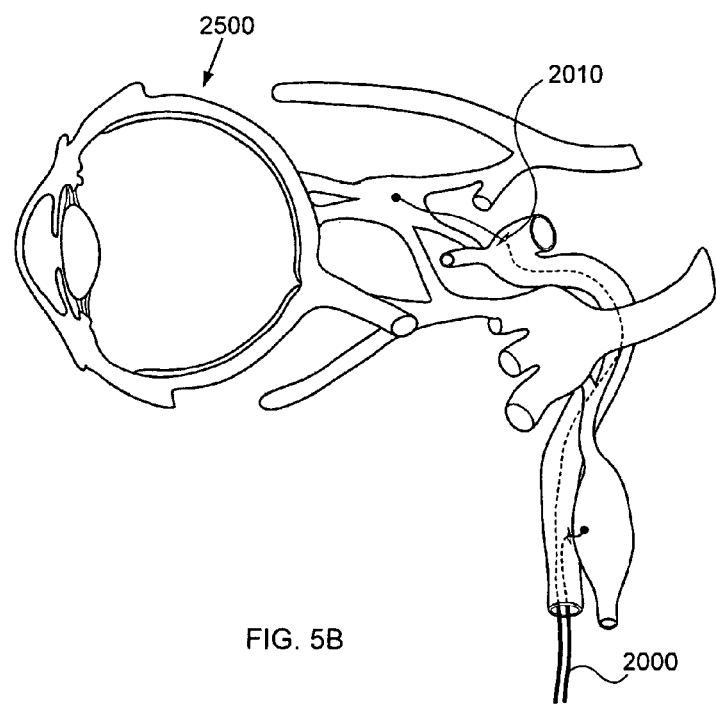

FIGS. 5a-b illustrates the eye in close up detail with sympathetic nerves surrounding the posterior of the eye. In the eye, glaucoma is a problem of world-wide import. The most commonly prescribed medication to treat glaucoma is timoptic, which is a non-selective β1 and β2 (adrenergic) antagonist. Compliance with this pharmaceutical is a major problem and limits its effectiveness in preventing the complications of glaucoma, the major complication being progression of visual dysfunction.

Ultrasound, or other energy transducers 700, can be applied to focus energy from an external region (e.g. a distance from the eye in an external location) anterior to the eye or to a region posteriorly behind the eye 2500 on the sympathetic 2010 or parasympathetic ganglia, all of which will affect lowering of intra-ocular pressure. The energy transducers 700 apply ablative or near ablative energy to the adventitia of the blood vessel.

FIG. 5b depicts the anatomy behind the eye. In this illustration, a catheter 2000 is tunneled through the vasculature to the region of the sympathetic nerves surrounding the arteries of the eye 2010 and utilized to ablate, stun, or otherwise modulate the efferent and/or afferent nerves through the wall of the vasculature.

Figure 6:
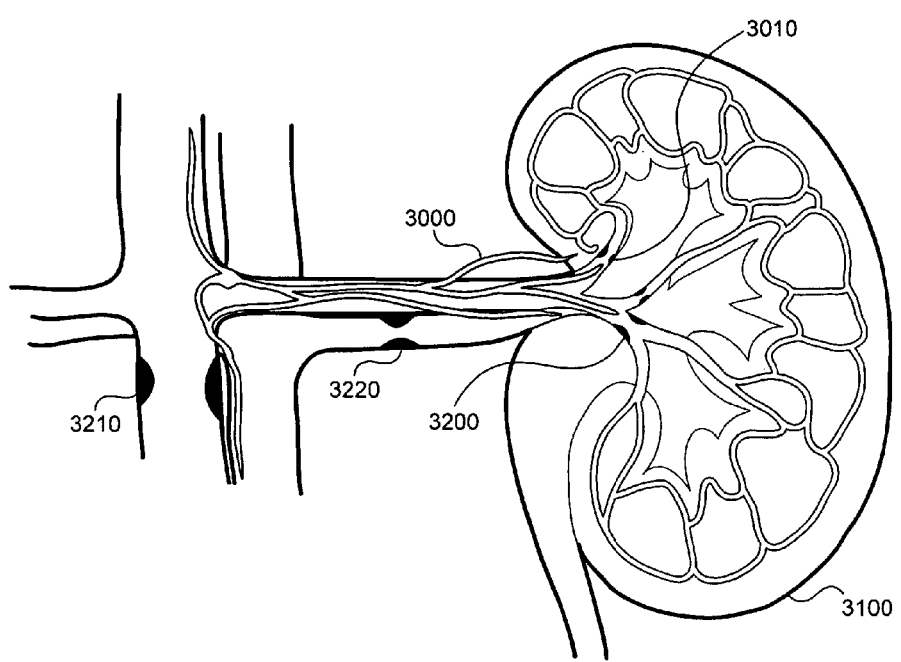
FIG. 6 depict the application of lesions to the kidney deep inside the calyces.

FIG. 6 illustrates an overall schematic of the renal artery collecting system. The individual nerves of the autonomic nervous system typically follow the body vasculature and they are shown in close proximity to the renal artery as the artery enters the kidney 3100 proper.

In one embodiment, selective lesions, constrictions or implants 3200 are placed in the calyces of the kidney to control or impede blood flow to specific regions of the kidney. Such lesions or implants can be placed on the arterial 3010 or venous sides 3220 of the kidney. In some embodiments, the lesions/implants are created so as to selectively block certain portions of the sympathetic nerves within the kidney. The lesions also may be positioned so as to ablate regions of the kidney which produce hormones, such as renin, which can be detrimental to a patient in excess. The implants or constrictions can be placed in the aorta 3210 or the renal vein 3220. In the renal vein, the implants can result in an increased pressure within the kidney to prevent the downward spiral of systolic heart failure described above. That is, once the pressure in the kidney is restored by increased venous pressure, the relative renal hypotension signaling to retain electrolytes and water will not be present any longer. In one embodiment, a stent which creates a stenosis is implanted using a catheter delivery system 3000. In another embodiment, a stricture is created using heat delivered either externally or internally.

Figure 7A:
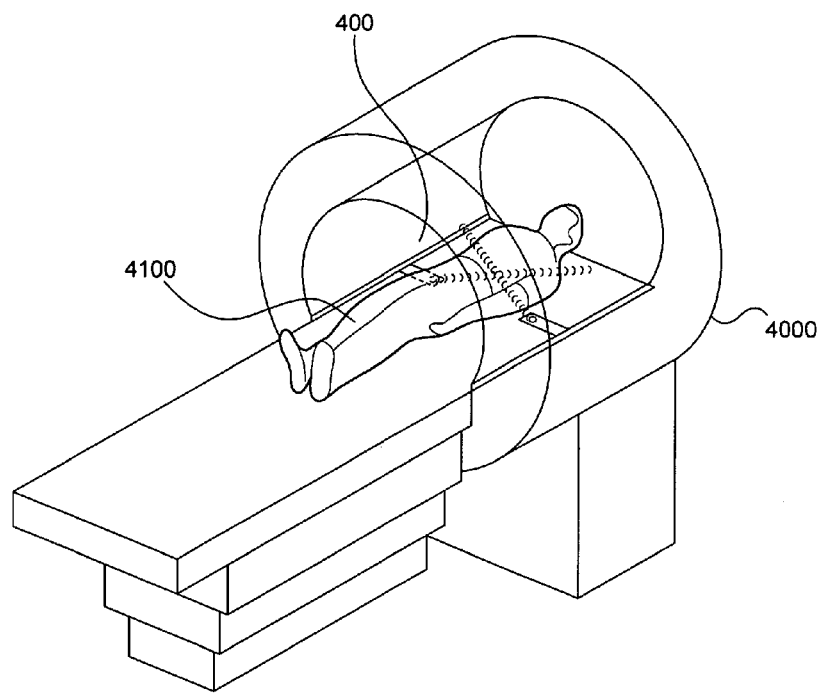
FIG. 7a depicts a patient in an imaging system receiving treating with focused energy waves.

FIG. 7a depicts at least partial ablation of the renal sympathetic nerves 4400 to the kidney using an imaging system such as an MRI machine or CT scanner 4000. The MRI/CT scan can be linked to a focused ultrasound (HIFU) machine to perform the ablations of the sympathetic nerves 4400 around the region of the renal artery 4500. The MRI/CT scan performs the imaging 4010 and transmits data (e.g. three dimensional representations of the regions of interest) to the ultrasound controller which then direct the ultrasound to target the region of interest with low intensity ultrasound (50-1000 mW/cm2) heat (>1000 mW/cm2), cavitation, or a combination of these modalities and/or including introduction of enhancing agents locally or systemically (sonodynamic therapy). Optionally, a doppler ultrasound or other 3D/4D ultrasound is performed and the data pushed to the MRI system to assist with localization of the pathology; alternatively, the ultrasound data are utilized to directly control the direction of the energy being used to target the physiologic processes and CT/MRI is not obtained. Using this imaging and ablation system from a position external to a patient, many regions of the kidney can be treated such as the internal calyces, the cortex, the medulla, the hilum and the region near to the aorta.

Further parameters which can be measured include temperature via thermal spectroscopy using MRI or ultrasound thermometry; thermal imaging is a well-known feature of MRI scanners; the data for thermal spectroscopy exists within the MRI scan and can be extrapolated from the recorded data in real time by comparing regions of interest before and after or during treatment. Temperature data overlaid on the MRI scan enables the operator of the machine to visualize the increase in temperature and therefore the location of the heating to insure that the correct region has indeed been ablated and that excessive energy is not applied to the region. Having temperature data also enables control of the ablation field as far as applying the correct temperature for ablation to the nerves. Furthermore, other spectroscopic parameters can be determined using the MRI scan such as oxygenation, blood flow, or other physiologic and functional parameters.

MRI scanners 4000 generally consist of a magnet and an RF coil. The magnet might be an electromagnet or a permanent magnet. The coil is typically a copper coil which generates a radiofrequency field. Recently, permanent magnets have been utilized to create scanners which are able to be used in almost any setting, for example a private office setting. Office based MRI scanners enable imaging to be performed quickly in the convenience of a physicians offices as well as requiring less magnetic force (less than 0.5 Tesla) and as a consequence, less shielding. The lower tesla magnets also provides for special advantages as far as diversity of imaging and resolution of certain features. Importantly, the permanent magnet MRI scanners are open scanners and do not encapsulate the patient during the scan.

In one embodiment, a permanent magnet MRI is utilized to obtain an MRI image of the region of interest 4010. High intensity focused 4100 ultrasound is used to target the region of interest 4600 identified using the MRI.

Image 4010 is monitored by a health care professional to ensure that the region of interest is being treated and can stop the therapy if the region is not being treated. Alternatively, an imaging algorithm can be initiated in which the region of interest is identified and then subsequent images are compared to the initial demarcated region of interest.

Perhaps, most importantly, with MRI, the region around the renal arteries can be easily imaged as can any other region such as the eye, brain, prostate, breast, liver, colon, spleen, aorta, hip, knee, spine, venous tree, and pancreas. The imaging from the MRI can be utilized to precisely focus the ultrasound beam to the region of interest around the renal arteries or elsewhere in the body. With MRI, the actual nerves to be modified or modulated can be directly visualized and targeted with the energy delivered through the body from the ultrasound transducers.

Figures 7B, 7C:
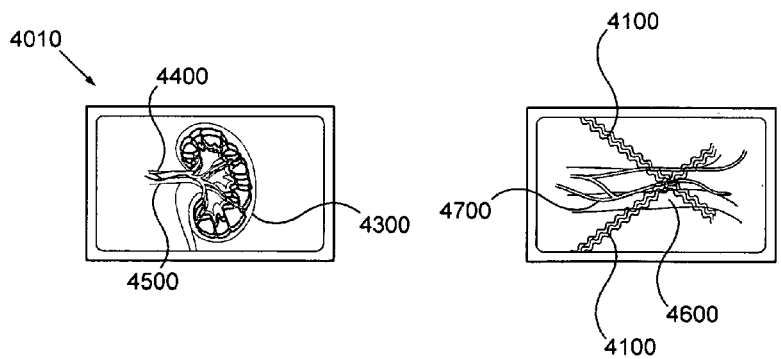
FIGS. 7b-d depict a method to treat the autonomic nervous system using MRI and energy transducers.
Figure 7D:
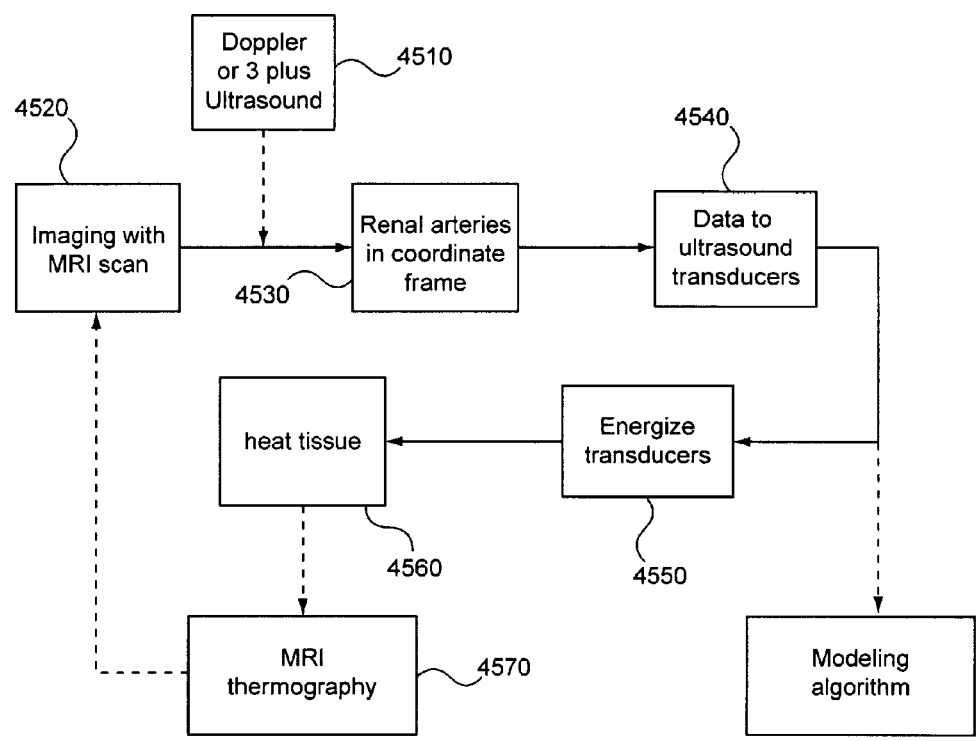

FIG. 7b depicts a method of treating a region with high intensity focused ultrasound (HIFU). Imaging with an MRI 4520 or Doppler ultrasound 4510 (or preferably both) is performed. MRI can be used to directly or indirectly (e.g. using functional MRI or spectroscopy) to visualize the sympathetic nerves. T1 weighted or T2 weighted images can be obtained using the MRI scanner. In addition to anatomic imaging, the MRI scanner can also obtain temperature data regarding the effectiveness of the ablation zone as well as the degree to which the zone is being heated and which parts of the zones are being heated. Other spectroscopic parameters can be added as well such as blood flow and even nerve activity. Ultrasound can be used to add blood flow to the images using Doppler imaging. The spectroscopic data can be augmented by imaging moieties such as particles, imaging agents, or particles coupled to imaging agents which are injected into the patient intravenously, or locally, and proximal to the region of the renal arteries; these imaging moieties may be visualized on MRI, ultrasound, or CT scan. Ultrasound can also be utilized to determine information regarding heating. The reflectance of the ultrasonic waves changes as the temperature of the tissue changes. By comparing the initial images with the subsequent images after heating, the temperature changes can be determined.

In one embodiment, the kidneys are detected by the cross-sectional imaging modality such as MRI, ultrasound, or CT scan. Next, the imaging data is placed into a three dimensional coordinate system which is linked to one or more ultrasound (e.g. HIFU) transducers which focus ultrasound onto the region of the renal arteries in the coordinate frame. The linking, or coupling, of the imaging to the therapeutic transducers is accomplished by determining the 3 dimensional position of the target by creating an anatomic model. The transducers are placed in a relative three dimensional coordinate frame as well. For example, the transducers can be placed in the imaging field during the MRI or CT scan such that the cross-sectional pictures include the transducers. Alternatively, ultrasound is utilized and the ultrasound image can be directly correlated to the origin of the imaging transducer. The therapeutic transducer in some embodiments is the same as the imaging transducer and therefore the therapeutic transducer is by definition coupled in a coordinate reference once the imaging transducer coordinates are known. If the therapeutic transducer and the imaging transducer are different devices, then they can be coupled by knowledge of the relative position of the two devices. The region of interest (ROI) is highlighted in a software algorithm . . . for example, the renal arteries, the calyces, the medullary region, the cortex, the renal hila, the celiac ganglia, the aorta, or any of the veins of the venous system as well. In another embodiment, the adrenal gland, the vessels traveling to the adrenal gland, or the autonomic nerves traveling to the adrenal gland are targeted with focused ultrasound and then either the medulla or the cortex of the adrenal gland or the nerves and arteries leading to the gland are partially or fully ablated with ultrasonic energy.

Once the transducers are energized after the region is targeted, the tissue is heated 4560 and a technique such as MRI thermography 4570 or ultrasound thermography is utilized to determine the tissue temperature. During the assessment of temperature, the anatomic data from the MRI scan or the Doppler is then referenced to ensure proper positioning and the degree of energy transduction is again further assessed by the modeling algorithm 4545 to set the parameters for the energy transducers 4550.

Ablation can also be augmented using agents such as magnetic nanoparticles or liposomal nanoparticles which are responsive to a radiofrequency field generated by a magnet. These particles can be selectively heated by the magnetic field. The particles can also be enhanced such that they will target specific organs and tissues using targeting moieties such as antibodies, peptides, etc. In addition to the delivery of heat, the particles can be activated to deliver drug or bioactive, or imaging agent at the region at which action is desired.

The addition of Doppler ultrasound 4510 may be provided as well. The renal arteries are (if renal arteries are the target) placed in a 3D coordinate reference frame 4530 using a software algorithm with or without the help of fiducial markers. Data is supplied to ultrasound transducers 4540 from a heat modeling algorithm 4545 and the transducers are energized with the appropriate phase and power to heat the region of the renal artery to between 40 degrees C. and 90 degrees C. within a time span of several minutes. The ultrasound transducers may have frequencies below 1 megahertz (MHz), from 1-20 MHz, or above 30 Mhz. The transducers may be in the form of a phased array, either linear or curved, or the transducers may be mechanically moved so as to focus ultrasound to the target of interest. In addition, MRI thermography 4570 can be utilized so as to obtain the actual temperature of the tissue being heated. These data can be further fed back to the system to slow down or speed up the process of ablation 4560 via the transducers 4550.

Aside from focused ultrasound, ultrasonic waves can be utilized directly to either heat an area or to activate pharmaceuticals in the region of interest. There are several methodologies to enhance drug delivery using focused ultrasound. For example, particles can release pharmaceutical when they are heated by the magnetic field. Liposomes can release a payload when they are activated with focused ultrasound. Ultrasound waves have a natural focusing ability if a transducer is placed in the vicinity of the target and the target contains an activateable moiety such as a bioactive drug or material (e.g. a nanoparticle sensitive to acoustic waves). Examples of sonodynamically activated moieties include some porphyrin derivatives.

So as to test the region of interest and the potential physiologic effect of ablation in that region, the region can be partially heated with the focused ultrasound to stun or partially ablate the nerves. Next, a physiologic test such as the testing of blood pressure or measuring norepinephrine levels in the blood can be performed to ensure that the correct region was indeed targeted for ablation.

In another embodiment, a fiducial is utilized to demarcate the region of interest. For example, the fiducial can be an implanted fiducial, a fiducial or device placed in the blood vessels, or a device placed percutaneously through a catheterization or other procedure. The fiducial can also be a bone, such as a rib, or another internal organ, for example, the liver. In one embodiment, the fiducial is a beacon or or balloon or balloon with a beacon which is detectable via ultrasound. In one embodiment, the blood flow in the renal arteries, detected via Doppler, is the fiducial and its relative direction is determined via Doppler analysis. Next, the renal arteries, and specifically, the region around the renal arteries are placed into a three dimensional coordinate frame utilizing the internal fiducials. A variant of global positioning system technology can be utilized to track the fiducials within the artery or around the arteries. The three dimensional coordinate frame is transmitted to the therapeutic ultrasound transducers and then the transducers and anatomy are coupled to the same coordinate frame.

Figure 17D:
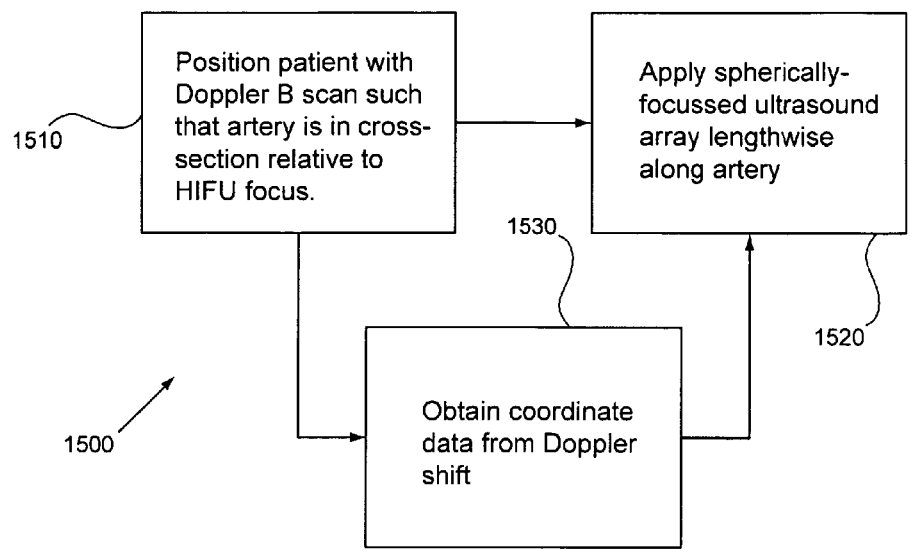

In one embodiment, a virtual fiducial is created. For example, in the case of a blood vessels such as the renal artery, an image of the blood vessel using ultrasound can be obtained which correlates to the blood vessel being viewed in direct cross section (1700; FIG. 17C). When the vessel is viewed in this type of view, the center of the vessel can be aligned with the center of an ultrasound array (e.g. HIFU array 1600) and the transducers can be focused and applied to the vessel, applying heat to regions around the vessels 1680. With different positions of the transducers 1610 along a circumference or hemisphere 1650, varying focal points can be created 1620, 1630, 1640. The directionality of the transducers allows for a lesion which runs lengthwise along the vessel 1620, 1630, 1640. Thus a longitudinal lesion can be produced along the artery to insure maximal inhibition of nerve function.

In this method of treatment, an artery such as a renal artery is viewed in cross-section or close to a cross-section under ultrasound guidance. In this position, the blood vessel is parallel to the axis of the spherical transducer to facilitate lesion production. The ultrasound transducers setup 1600 has previously been calibrated to create focal lesions 1620, 1630, 1640 along the artery if the artery is in cross-section 1680.

In one embodiment, the fiducial is an intravascular fiducial such as a balloon. The balloon is detectable via radiotransmitter within the balloon which is detectable by the external therapeutic transducers. The balloon can have three transducers, each capable of relaying their position so that the balloon can be placed in a three dimensional coordinate reference. Once the balloon is placed into the same coordinate frame as the external transducers using the transmitting beacon, the energy transducing devices can deliver energy (e.g. focused ultrasound) to the blood vessel (e.g. the renal arteries) or the region surrounding the blood vessels (e.g. the renal nerves). The balloon and transmitters also enable the ability to definitively track the vasculature in the case of movement (e.g. the renal arteries). In another embodiment, the balloon measures temperature or is a conduit for coolant applied during the heating of the artery or nerves.

Delivery of therapeutic ultrasound energy is delivered to the tissue inside the body via ultrasound transducers directed to deliver energy to the target in the coordinate frame.

Once the target is placed in the coordinate frame and the energy delivery is begun, it is important to maintain targeting of the position, particularly when the target is a small region such as the sympathetic nerves. To this end, the position of the region of ablation is compared to its baseline position. The ongoing positional monitoring and information is fed into an algorithm which determines the new targeting of the energy waves at the target. In one embodiment, if the position is too far from the original position, then the energy delivery is stopped and the patient repositioned. If the position is not too far from the original position, then the energy transducers can be repositioned either mechanically (e.g. through physical movement) or electrically via phased array (e.g. by changing the relative phase of the waves emanating from the transducers). In another embodiment, multiple transducers are placed on the patient in different positions and each is turned on or off to result in the necessary energy delivery.

In addition to heat delivery, ultrasound can be utilized to deliver cavitating energy which may enable drug delivery at certain frequencies. Cavitating energy can also lead to ablation of tissue at the area of the focus. A systemic dose of a drug can be delivered to the region of interest and the region targeted with the cavitating or other forms of ultrasonic energy. Other types of therapeutic delivery modalities include ultrasound sensitive bubbles or radiation sensitive nanoparticles, all of which enhance the effect of the energy at the target of interest.

Ultrasound may also be utilized to create tumor vaccines in vivo. In this embodiment, sub-ablative doses of energy is applied to a tumor to induce a stress response or to heat shock response to increase the anti-tumor or immune response to the tumor.

Figure 8A:
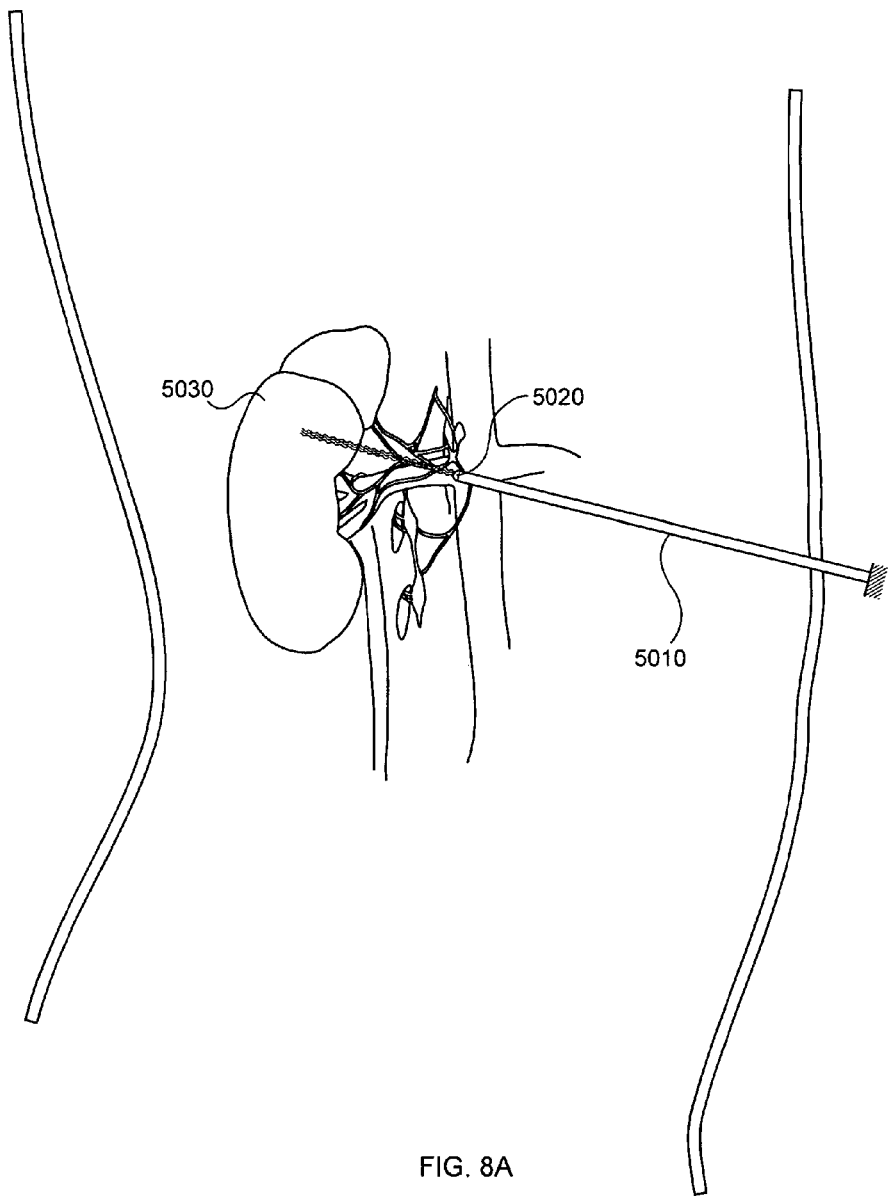
FIG. 8a depicts a percutaneous approach to treating the autonomic nervous system surrounding the kidneys.

FIG. 8a depicts a percutaneous procedure 5000 and device 5010 in which the region around the renal artery 5030 is approached through the skin and from an external position. A combination of imaging and ablation may be performed to ablate the region around the renal artery to treat hypertension, end stage renal disease, and heart failure. Probe 5010 is positioned through the skin and in proximity to the kidney 5030. The probe may include sensors which detect heat or temperature or may enable augmentation of the therapeutic energy delivery. Ablative, ionizing energy, heat, or light may be applied to the region to inhibit the sympathetic nerves around the renal artery using the probe 510. Ultrasound, radiofrequency, microwave, direct heating elements, and balloons with heat or energy sources may be applied to the region of the sympathetic nerves. In one embodiment, the percutaneous procedure is performed under MRI, CT, or ultrasound guidance to obtain localization or information about the degree of heat being applied. A particularly preferred embodiment would be to perform the procedure under guidance from an MRI scanner because the region being heated can be determined anatomically in real time as well via temperature maps. As described above the images after heating can be compared to those at baseline and the signals are compared at the different temperatures.

In one embodiment, selective regions of the kidney are ablated through the percutaneous access route; for example, regions which secrete hormones which are detrimental to a patient or to the kidneys or other organs. Using energy applied external to the patient through the skin and from different angles affords the ability to target any region in or on the kidney or along the renal nerves or at the region of the adrenal gland, aorta, or sympathetic chain. This greater breadth in the number of regions to be targeted is enabled by the combination of external imaging and external delivery of the energy from a multitude of angles through the skin of the patient to the target.

In a further embodiment, probe 5010 can be utilized to detect temperature or motion of the region while the ultrasound transducers are applying the energy to the region. A motion sensor, position beacon, or accelerometer can be used to provide feedback for the HIFU transducers. In addition, an optional temperature or imaging modality may be placed on the probe 5010. The probe 5010 can also be used to locate the position within the laparoscopic field for the ablations to be performed.

Figure 8B:
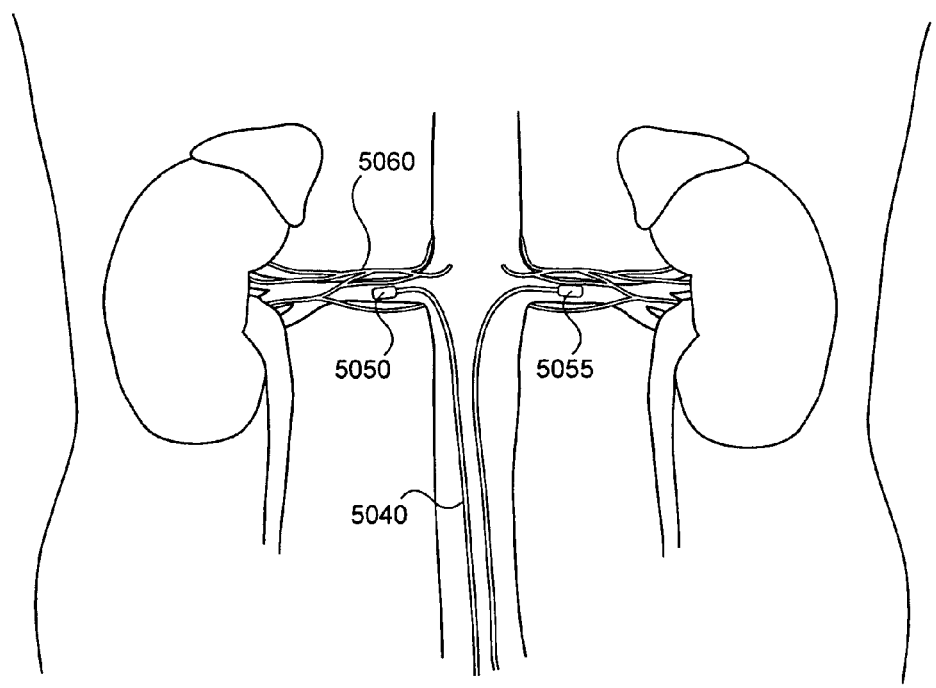
FIG. 8b depicts an intravascular approach to treating the autonomic nervous system.

In FIG. 8b an intravascular device 5050 is depicted which applies energy to the region around the renal arteries 5055, 5060. The intravascular devices can be utilized to apply radiofrequency, ultrasound (either focused or unfocused) energy to the renal artery and surrounding regions. MRI or ultrasound or direct thermometry can be further utilized to detect the region where the heat is being applied while the intravascular catheter is in place.

Alternatively, in another embodiment, the devices 5050, 5055 can be utilized to direct the ultrasound to the correct place around the artery as the HIFU transducers deliver the energy to the region. For example, the intravascular probe 5050 can be utilized as a homing beacon for the imaging technology utilized for the externally delivered HIFU.

Figure 9A:
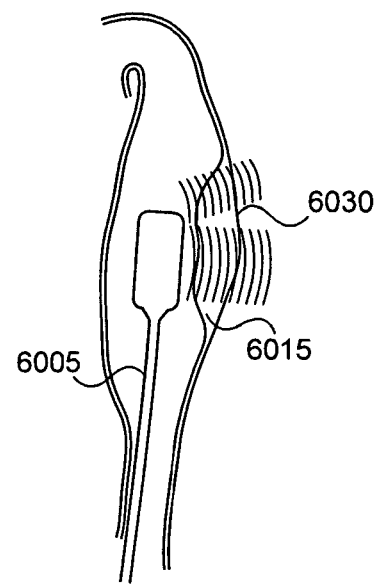
FIGS. 9a-c depicts the application of energy from inside the aorta to regions outside the aorta.

In another embodiment, the physiologic process of arterial expansion is targeted. In FIG. 9a, an ultrasound transducer is 6005 is placed near the wall of an aneurysm 6030. Ultrasonic energy is applied to the wall 6030 of the aneurysm to thicken the wall and prevent further expansion of the aneurysm. In some embodiments, clot within the aneurysm is targeted as well so that the clot is broken up or dissolved with the ultrasonic energy. Once the wall of the aneurysm is heated with ultrasonic energy to a temperature of between 40 and 70 degrees, the collagen, elastin, and other extracellular matrix in the wall will harden as it cools, thereby preventing the wall from further expansion. In another embodiment, a material is placed in the aneurysm sac and the focused or non-focused ultrasound utilized to harden or otherwise induce the material in the sac to stick to the aorta or clot in the aneurysm and thus close the aneurysm permanently. In one embodiment therefore, an ultrasound catheter is placed in an aorta at the region of an aneurism wall or close to a material in an aneurysmal wall. The material can be a man-made material placed there by an operator or it can be material such as thrombus which is in the aneurysm naturally. Ultrasound is applied to the wall, or the material, resulting in hardening of the wall or of the material, strengthening the aneurysm wall and preventing expansion.

Figure 9B:
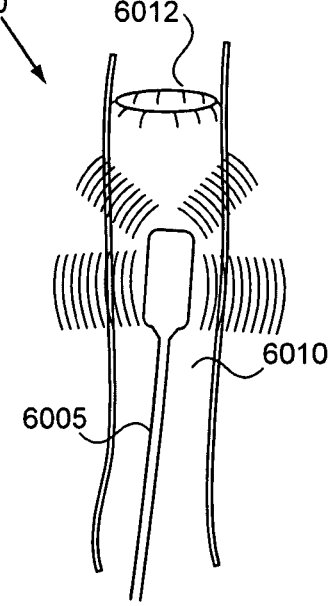

FIG. 9b depicts a clot prevention device 6012 within a blood vessel such as the aorta or vena cava 6000. The ultrasound catheter 6005 is applied to the clot prevention device (filter) 6012 so as to remove the clot from the device or to free the device 6012 from the wall of the blood vessel in order to remove it from the blood vessel 6000.

Figure 9C:
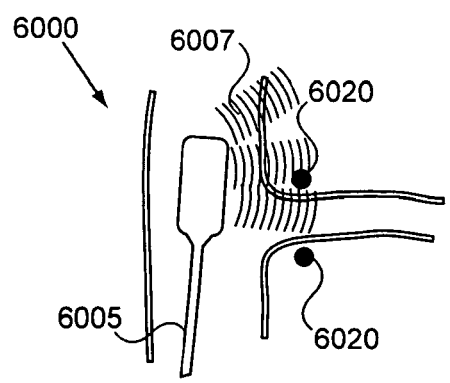

FIG. 9c depicts a device and method in which the celiac plexus 6020 close to the aorta 6000 is ablated or partially heated using heat energy from an ultrasonic energy source 6005 which can apply focused or unfocused sound waves 6007 at frequencies ranging from 20 kilohertz to 5 Mhz. Full, or partial ablation of the celiac plexus 6020 can result in a decrease in blood pressure via a similar mechanism as in FIG. 9; the ablation catheter is a focused ultrasound catheter but can also be a direct ultrasound, a microwave element, or a resistive heating element.

Figure 10:
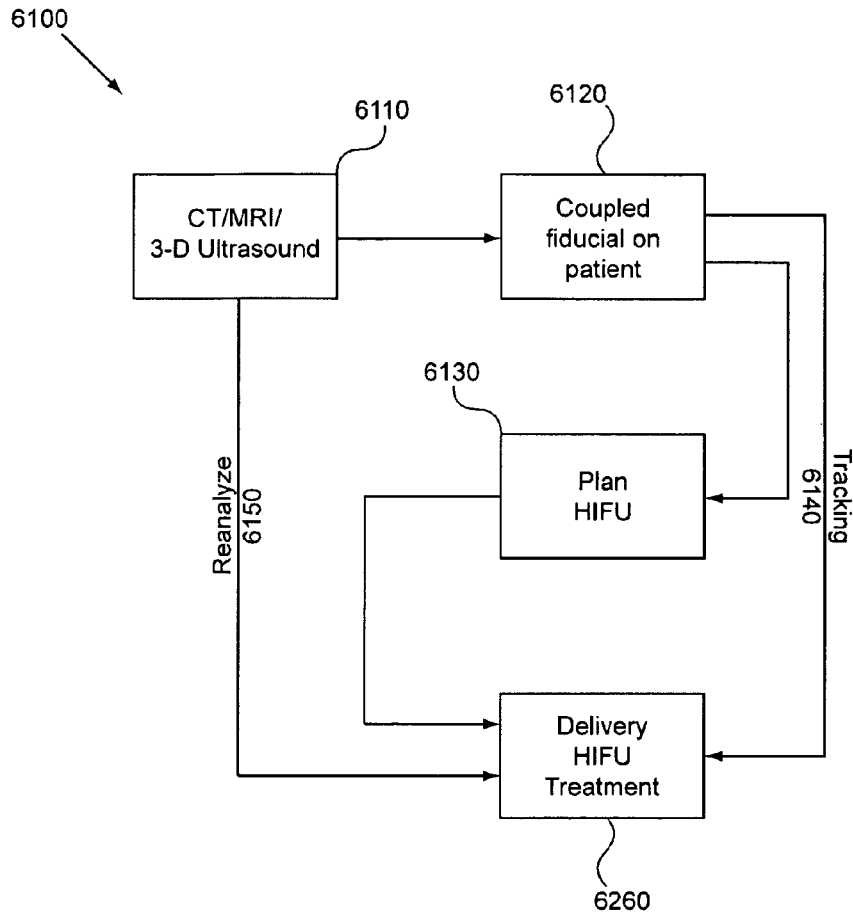
FIG. 10 depicts steps to treat a disease using HIFU.

FIG. 10 depicts a method 6100 to treat a patient with high intensity focused ultrasound (HIFU) 6130. In a first step, a CT and/or MRI scan and/or thermography and/or 3D ultrasound is performed 6110. A fiducial or other marking on the patient 6120 is optionally used to mark and track the patient. The fiducial can be an implanted fiducial, a temporary fiducial, or a fiducial intrinsic to the patient (e.g. bone) which can be imaged using the CT/MRI/Ultrasound devices 6010. The fiducial can further be a temporary fiducial such as a catheter temporarily placed in an artery or vein of a patient or a percutaneously placed catheter. A planning step 6130 for the HIFU treatment is performed in which baseline readings such as position of the organ and temperature are determined; a HIFU treatment is then planned using a model (e.g. finite element model) to predict heat transfer, or pressure to heat transfer, from the ultrasound transducers 6130.

The planning step 6130 includes determination of the positioning of the ultrasound transducers as far as position of the focus in the patient. X,Y,Z, and three angular coordinates are used to determine the position of the ultrasonic focus in the patient based on the cross sectional imaging 6110. The HIFU transducers might have their own position sensors built in so that the position relative to the target can be assessed. Alternatively, the HIFU transducers can be rigidly fixed to the table on which the patient rests so that the coordinates relative to the table and the patient are easily obtainable. The flow of heat is also modeled in the planning step 6130 so that the temperature at a specific position with the ultrasound can be planned and predicted. For example, the pressure wave from the transducer is modeled as it penetrates through the tissue to the target. For the most part, the tissue can be treated as water with a minimal loss due to interfaces. The relative power and phase of the ultrasonic wave at the target can be determined by the positional coupling between the probe and target. A convective heat transfer term is added to model heat transfer due to blood flow, particularly in the region of an artery. A conductive heat transfer term is also modeled in the equation for heat flow and temperature.

Another variable which is considered in the planning step is the size of the lesion and the error in its position. In the ablation of small regions such as nerves surrounding blood vessels, the temperature of the regions may need to be increased to a temperature of 60-90 degrees Celsius to permanently ablate nerves in the region. Temperatures of 40-60 degrees may temporarily inhibit or block the nerves in these regions and these temperatures can be used to determine that a patient will respond to a specific treatment without permanently ablating the nerve region.

An error analysis is also performed during the treatment. Each element of temperature and position contains an error variable which propagates through the equation of the treatment. The errors are modeled to obtain a virtual representation of the temperature mapped to position. This map is correlated to the position of the ultrasound transducers in the treatment of the region of interest.

During the delivery of the treatment 6200, the patient may move, in which case the fiducials 6120 track the movement and the position of the treatment zone is re-analyzed 6150 and the treatment is restarted or the transducers are moved either mechanically or electrically to a new focus position.

In another embodiment, a cross-sectional technique of imaging is used in combination with a modality such as ultrasound to create a fusion type of image. The cross-sectional imaging is utilized to create a three dimensional data set of the anatomy. The ultrasound, providing two dimensional images, is linked to the three dimensional imaging provided by the cross-sectional machine through fiducial matches between the ultrasound and the MRI. As a body portion moves within the ultrasound field, the corresponding data is determined (coupled to) the cross-sectional (e.g. MRI image) and a viewing station can show the movement in the three dimensional dataset. The ultrasound provides real time images and the coupling to the MRI or other cross-sectional image depicts the ultrasound determined position in the three dimensional space.

FIG. 11 depicts the treatment of another disease in the body of a patient, this time in the head of a patient. Subdural and epidural hematomas occur as a result of bleeding of blood vessels in the dural or epidural spaces of the brain, spinal column, and scalp. FIG. 11 depicts a CT or MRI scanner 7300 and a patient 7400 therein. An image is obtained of the brain 7000 using a CT or MRI scan. The image is utilized to couple the treatment zone 7100 to the ultrasound arrays utilized to heat the region. In one embodiment 7100, a subdural hematoma, either acute or chronic, is treated. In another embodiment 7200, an epidural hematoma is treated. In both embodiments, the region of leaking capillaries and blood vessels are heated to stop the bleeding, or in the case of a chronic subdural hematoma, the oozing of the inflammatory capillaries.

In an exemplary embodiment of modulating physiologic processes, a patient 7400 with a subdural or epidural hematoma is chosen for treatment and a CT scan or MRI 7300 is obtained of the treatment region. Treatment planning ensues and the chronic region of the epidural 7200 or subdural 7010 hematoma is targeted for treatment with the focused ultrasound 7100 transducer technology. Next the target of interest is placed in a coordinate reference frame as are the ultrasound transducers. Therapy 7100 ensues once the two are couple together. The focused ultrasound heats the region of the hematoma to dissolve the clot and/or stop the leakage from the capillaries which lead to the accumulation of fluid around the brain 7420. The technology can be used in place of or in addition to a burr hole, which is a hole placed through the scalp to evacuate the fluid.

Figure 12:
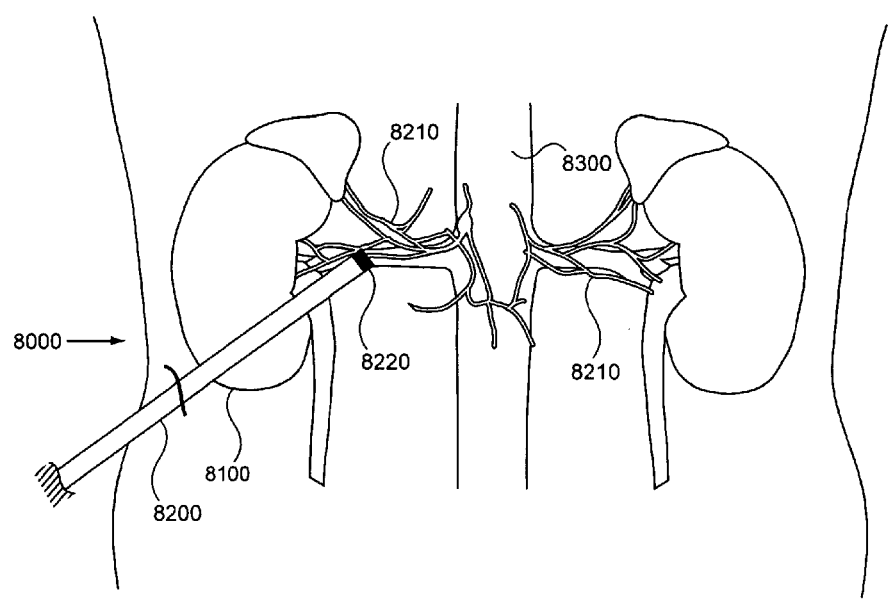
FIG. 12 depicts treatment of the renal nerve region using a laparoscopic approach.

FIG. 12 depicts a laparoscopic based approach 8000 to the renal artery region in which the sympathetic nerves 8210 can be ligated, interrupted, or otherwise modulated. In laparoscopy, the abdomen of a patient is insufflated and laparoscopic instruments introduced into the insufflated abdomen. The retroperitoneum is accessible through a flank approach or through a transabdominal approach. A laparoscopic instrument 8200 with a distal tip 8220 can apply heat or another form of energy or deliver a drug to the region of the sympathetic nerves 8210. The laparoscopic implement can also be utilized to ablate or alter the region of the celiac plexus 8300 and surrounding ganglia. The laparoscope can have an ultrasound transducer attached, a temperature probe attached, a microwave transducer attached, or a radiofrequency transducer attached. The laparoscope can be utilized to directly ablate or stun the nerves surrounding vessels or can be used to ablate or stun nerve ganglia which travel with the blood vessels.

Figure 13:
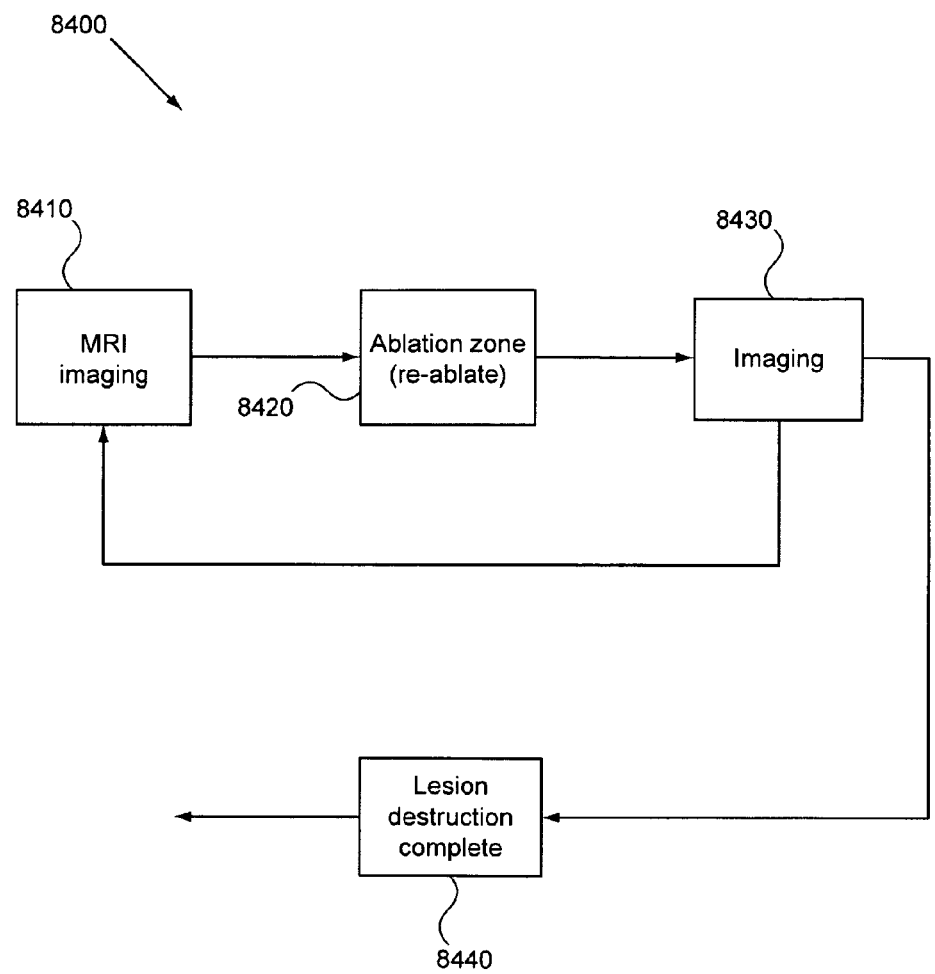
FIG. 13 depicts a methodology for destroying a region of tissue using imaging markers.

FIG. 13 depicts an algorithm for the treatment of a region of interest. MRI and/or CT with or without a imaging agent 8410 can be utilized to demarcate the region of interest (for example, the ablation zone) and then ablation 8420 can be performed around the zone identified by the agent using any of the modalities above. This algorithm is applicable to any of the therapeutic modalities described above including external HIFU, laparoscopic instruments, intravascular catheters, percutaneous catheters, as well as any of the treatment regions including the renal nerves, the eye, the kidneys, the aorta, or any of the other nerves surrounding peripheral arteries or veins. Imaging 8430 with CT, MRI, ultrasound, or PET can be utilized in real time. At such time when destruction of the lesion is complete 8440, imaging with an imaging (for example, a molecular imaging agent or a contrast agent such as gadolinium) agent 8410 can be performed again. The extent of ablation can also be monitored by monitoring the temperature or the appearance of the ablated zone under an imaging modality. Once lesion destruction is complete 8440, the procedure is finished.

Figure 14:
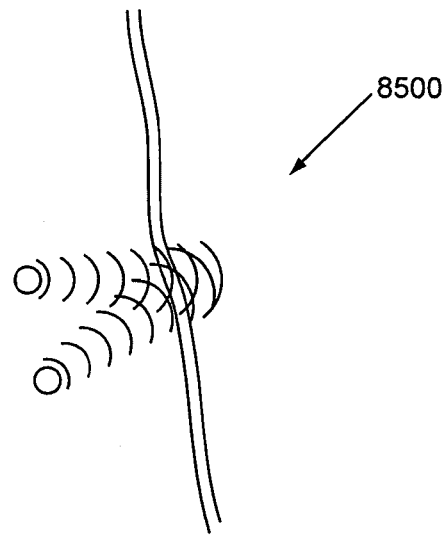
FIG. 14 depicts the partial treatment of a nerve bundle using converging imaging waves.

FIG. 14 depicts ablation in which specific nerve fibers of a nerve are targeted using different temperature gradients or temperatures 8500. For example, if temperature is determined by MRI thermometry or with another technique such as ultrasound, then the temperature can be kept at a temperature in which only certain nerve fibers are targeted for destruction or inhibition. Alternatively, part or all of the nerve can be turned off temporarily to then test the downstream effect of the nerve being turned off. For example, the sympathetic nerves around the renal artery can be turned off with a small amount of heat or other energy and then the effect can be determined. For example, norepinephrine levels in the blood or the stimulation effect of the nerves can be tested after temporary cessation of activity.

Figure 15:
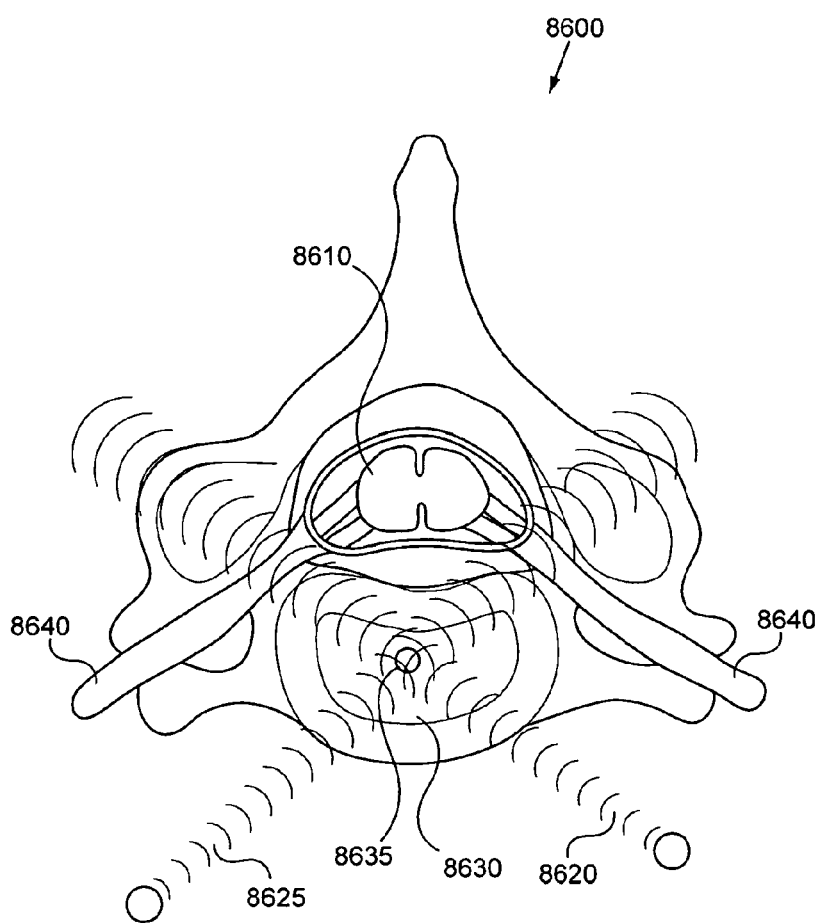
FIG. 15 depicts the application of focused energy to the vertebral column.

FIG. 15 depicts treatment 8600 of a vertebral body or intervertebral disk 8610 in which nerves within 8640 or around the vertebral column 8630 are targeted with ultrasound 8625 waves. In one embodiment, nerves around the facet joints are targeted. In another embodiment, nerves leading to the disks or vertebral endplates are targeted.

Figure 16:
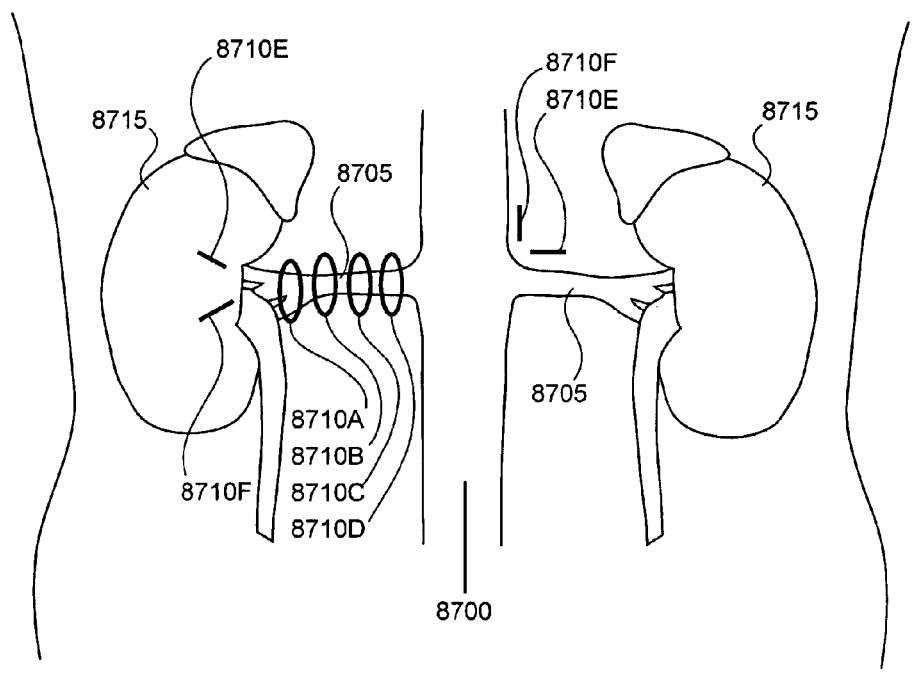
FIG. 16 depicts the types of lesions which are created around the renal arteries to affect a response.

FIG. 16 depicts a set of lesion types, sizes, and anatomies 8710a-h which lead to de-innervation of the different portions of the sympathetic nerve tree. For example, the lesions can be annular, cigar shaped, linear, doughnut and/or spherical; the lesions can be placed around the renal arteries 8705, inside the kidney 8710, and/or around the aorta 8700. For example, the renal arterial tree 8700 comprises renal arteries 8705 and kidneys 8715. Lesions 8710a-h are different types of lesions which are created around the aorta 8700 and vascular tree.

FIG. 17a depicts a multi-transducer HIFU device 1100 which applies a finite lesion 1150 along an artery 1140 (e.g. a renal artery) leading to a kidney 1130. The lesion can be spherical in shape, cigar shaped 1050, annular shaped 1050, or point shaped; however, in a preferred embodiment, the lesion runs along the length of the artery and has a cigar shaped. This lesion is generated by a spherical type of ultrasound array in a preferred embodiment. FIG. 17c depicts the pathway of the spherical or cylindrical type of ultrasound array 1600. Ultrasound transducers 1610 are aligned along the edge of a cylinder aimed so that they intersect at one or more focal spots 1620, 1630, 1640. The transducers 1610 are positioned along the cylinder 1650 such that some are closer to one focus or the other so that a range of distances to the artery is created. The patient and artery are positioned such that their centers 1700 co-localize with the center of the ultrasound array 1600. Once the centers are co-localized, the HIFU energy can be activated to create lesions along the length of the artery wall 1640, 1620, 1630 at different depths and positions around the artery. The natural focusing of the transducers positioned along a cylinder as in FIG. 17b is a lengthwise lesion, longer than in thickness or height, which will run along the length of an artery when the artery is placed along the center axis of the cylinder. When viewed along a cross section the nerve ablations are positioned along a clock face 1680 around the vessel.

Importantly, during treatment, a treatment workstation 1300 gives multiple views of the treatment zone with both physical appearance and anatomy 1050. Physical modeling is performed in order to predict lesion depth and the time to produce the lesion; this information is fed back to the ultrasound transducers 1100. The position of the lesion is also constantly monitored in a three dimensional coordinate frame and the transducer focus at lesions center 1150 continually updated.

In some embodiments, motion tracking prevents the lesion or patient from moving too far out of the treatment zone during the ablation. If the patient does move outside the treatment zone during the therapy, then the therapy can be stopped.

Figure 18:
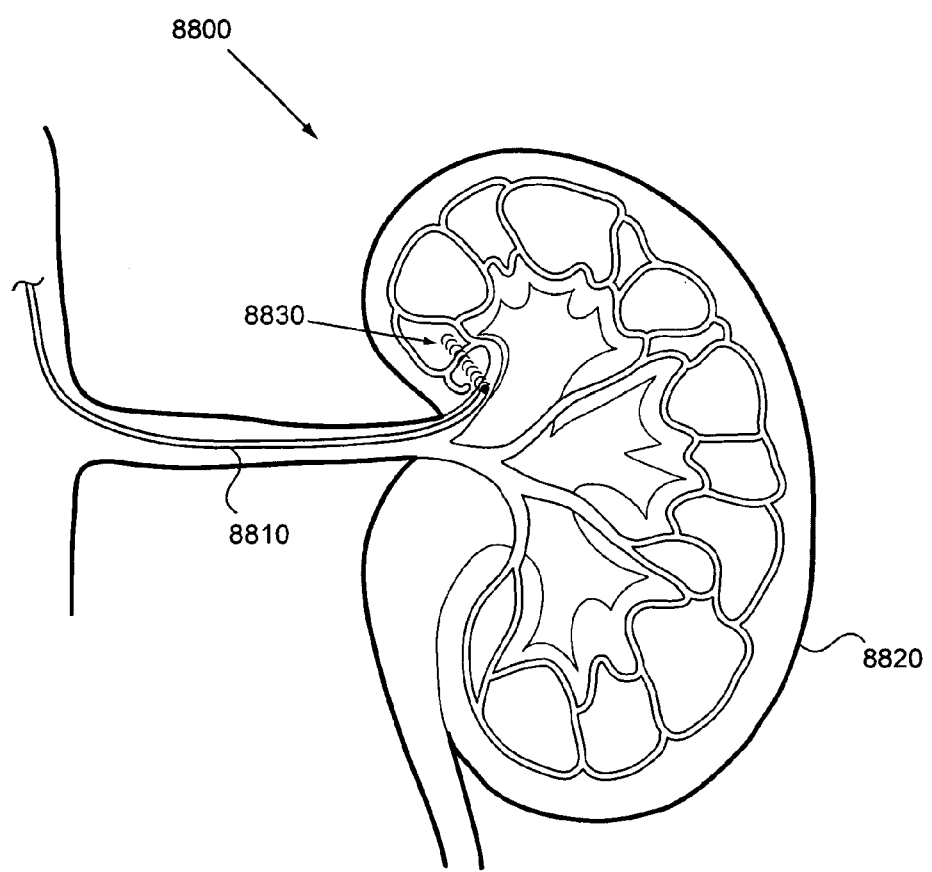
FIG. 18 depicts the application of energy internally within the kidney.

FIG. 18 depicts a micro-catheter 8810 which can be placed up into renal calyces 8820; this catheter allows the operator to specifically ablate or stimulate 8830 regions of the kidney 8800. The catheter can be used to further allow for targeting of the region around the renal arteries and kidneys by providing additional imaging capability or by assisting in movement tracking or reflection of the ultrasound waves to create or position the lesion. The catheter or device at or near the end of the catheter may transmit signals outside the patient to direct an energy delivery device which delivers energy through the skin.

In one method, a micro catheter is delivered to the renal arteries and into the branches of the renal arteries in the kidney. A signal is generated from the catheter into the kidney and out of the patient to an energy delivery system. Based on the generated signal, the position of the catheter in a three dimensional coordinate reference is determined and the energy source is activated to deliver energy to the region indicated by the microcatheter.

Alternatively, specific regions of the kidney might be responsible for hormone excretion or other factors which lead to hypertension or other detrimental effects to the cardiovascular system.

Figure 17E:
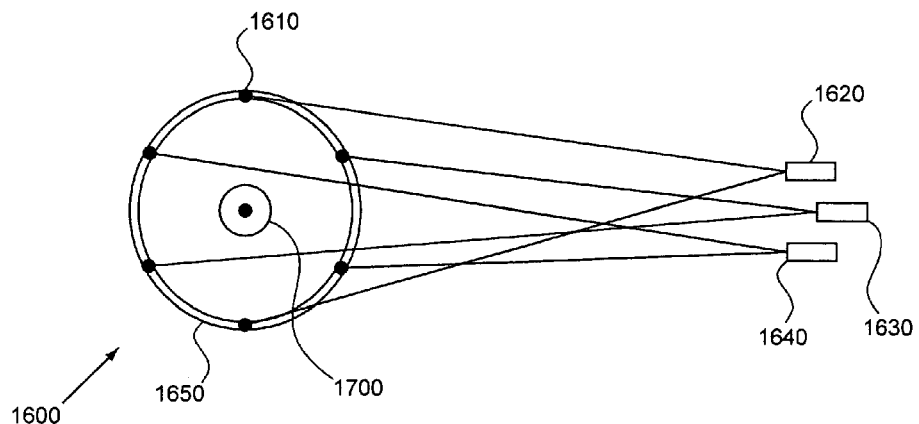
Figure 17F:
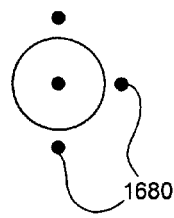
Figure 19:
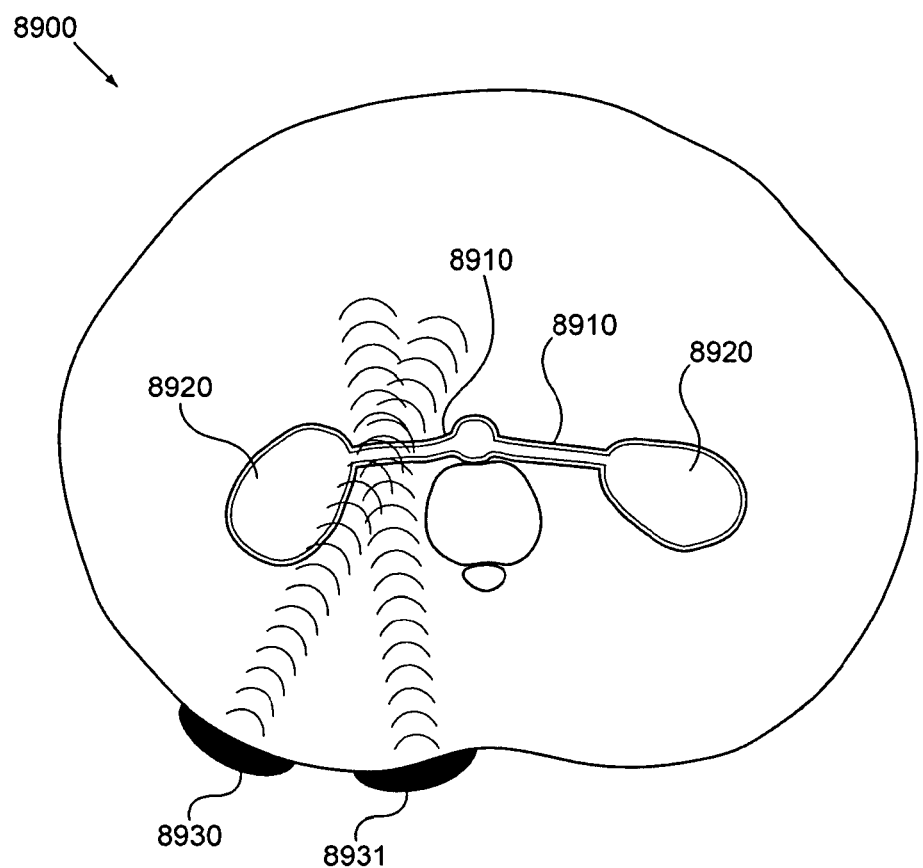
FIG. 19 depicts the direction of energy wave propagation to treat regions of the autonomic nervous system around the kidney region.

FIG. 19 depicts the application of acoustic waves to the region of the renal artery 8910 and kidney 8920 using physically separated transducers 8930, 8931. In contrast to the delivery method of FIG. 17, FIG. 19 depicts delivery of ultrasound transverse to the renal arteries and not longitudinal to the artery. In some embodiments, such delivery might be advantageous if for example, a longitudinal view of the artery is unobtainable or a faster treatment paradigm is desirable. The transducers 8930, 8931 communicate with one another and are connected to a computer model of the region of interest being imaged (ROI), the ROI based on an MRI scan performed just prior to the start of the procedure and throughout the procedure.

Figure 20:
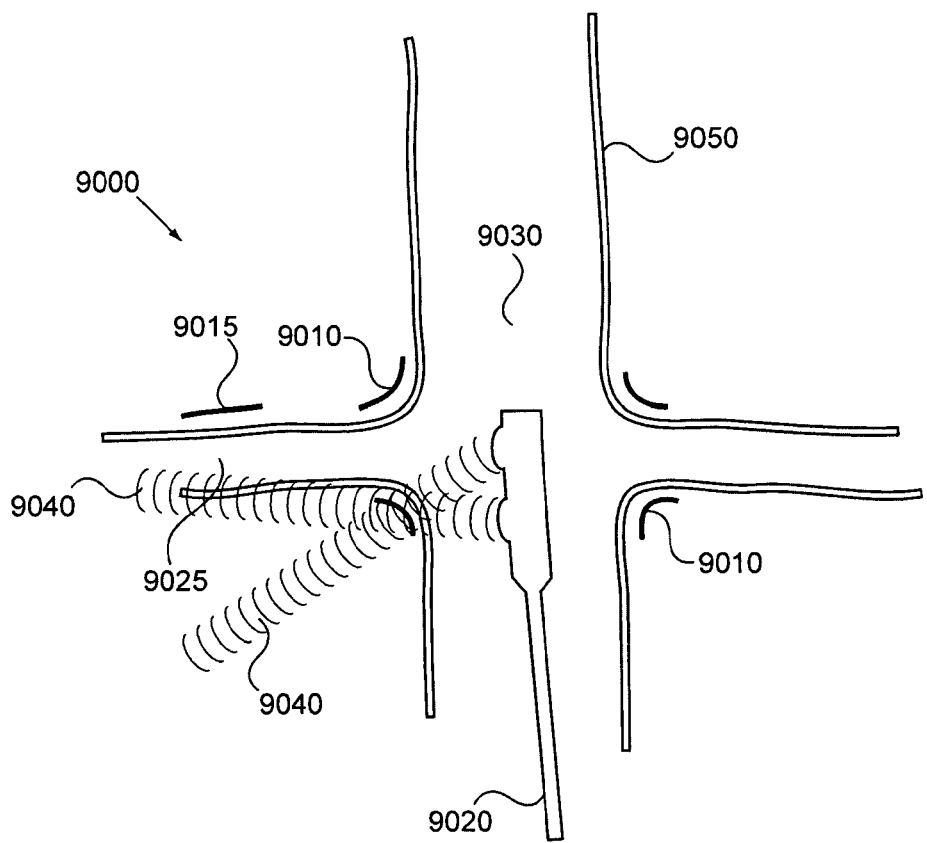
FIG. 20 depicts the application of ultrasound waves through the wall of the aorta

FIG. 20 depicts an alternative method 9000 and device to ablate the renal nerves 9015 or the nerves leading to the renal nerves at the aorta-renal artery osmium 9010. The intravascular device 9020 is placed into the aorta 9050 and advanced to the region of the renal arteries 9025. Energy is applied from the transducer 9020 and focused 9040 (in the case of HIFU) to the region of the takeoff of the renal arteries 9025 from the aorta 9050. This intravascular procedure can be guided using MRI and/or MRI thermometry or it can be guided using fluoroscopy, ultrasound, or MRI. Because the aorta is larger than the renal arteries, the HIFU catheter can be placed into the aorta directly. In addition, non-focused ultrasound can be applied to the region around the renal ostium or higher in the aorta. Non-focused ultrasound in some embodiments may require cooling of the tissues surrounding the probe using one or more coolants but in some embodiments, the blood of the aorta will take the place of the coolant; HIFU, or focused ultrasound, may not need the cooling because the waves are by definition focused from different angles to the region around the aorta. The vena cava can also be used as a conduit for the focused ultrasound transducer to deliver energy to the region.

Figure 21A:
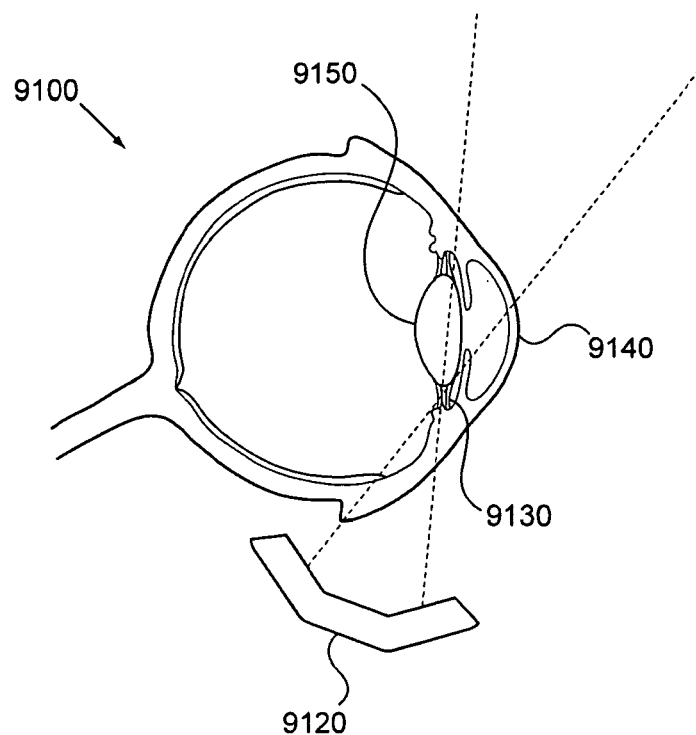
FIG. 21a depicts application of focused energy to the ciliary muscles and processes of the eye.
Figure 21B:
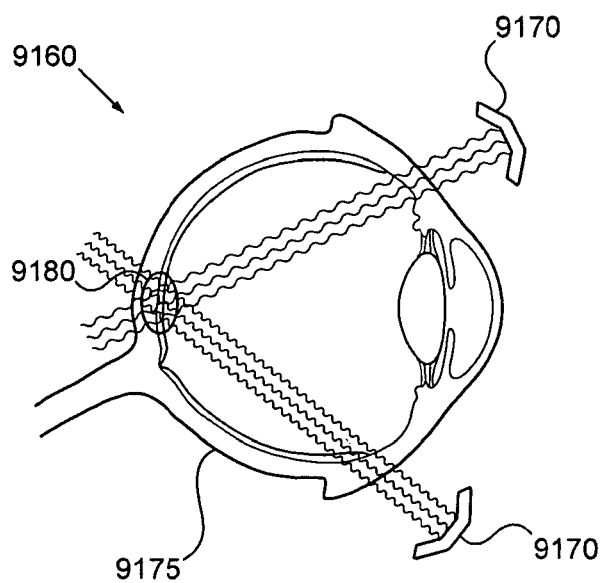
FIG. 21b depicts the application of focused non-ablative energy to the back of the eye to enhance drug or gene delivery or another therapy such as ionizing radiation.

FIG. 21 depicts an eyeball 9100. Also depicted are the zonules 9130 and ultrasound transducer 9120. The transducer 9120 applies focused ultrasound energy to the region surrounding the zonules, or the zonules themselves, in order to tighten them such that a presbyopic patient can accommodate. Similarly, heat to ciliary muscles, which then slows down the outflow of aqueous humor at the region of interest so that the pressure within the eye cannot build up to a high level. The ultrasound transducer 9120 can also be utilized to deliver drug therapy to the region of the lens, ciliary body, zonules, intravitreal cavity, anterior cavity, posterior cavity, etc.

In some embodiments (FIG. 21b), the ultrasonic transducers 9170 are focused on the particular region of the eye so that tissues along the path of the ultrasound are not damaged by the ultrasound and the focus region and region of effect is the position where the waves meet in the eye. In one embodiment, the transducers are directed through the pars plana region of the eye to target the macula 9180 at the posterior pole 9175 of the eye. This configuration might allow for heat, vibratory stimulation, drug delivery, gene delivery, augmentation of laser or ionizing radiation therapy, etc.

Figure 22:
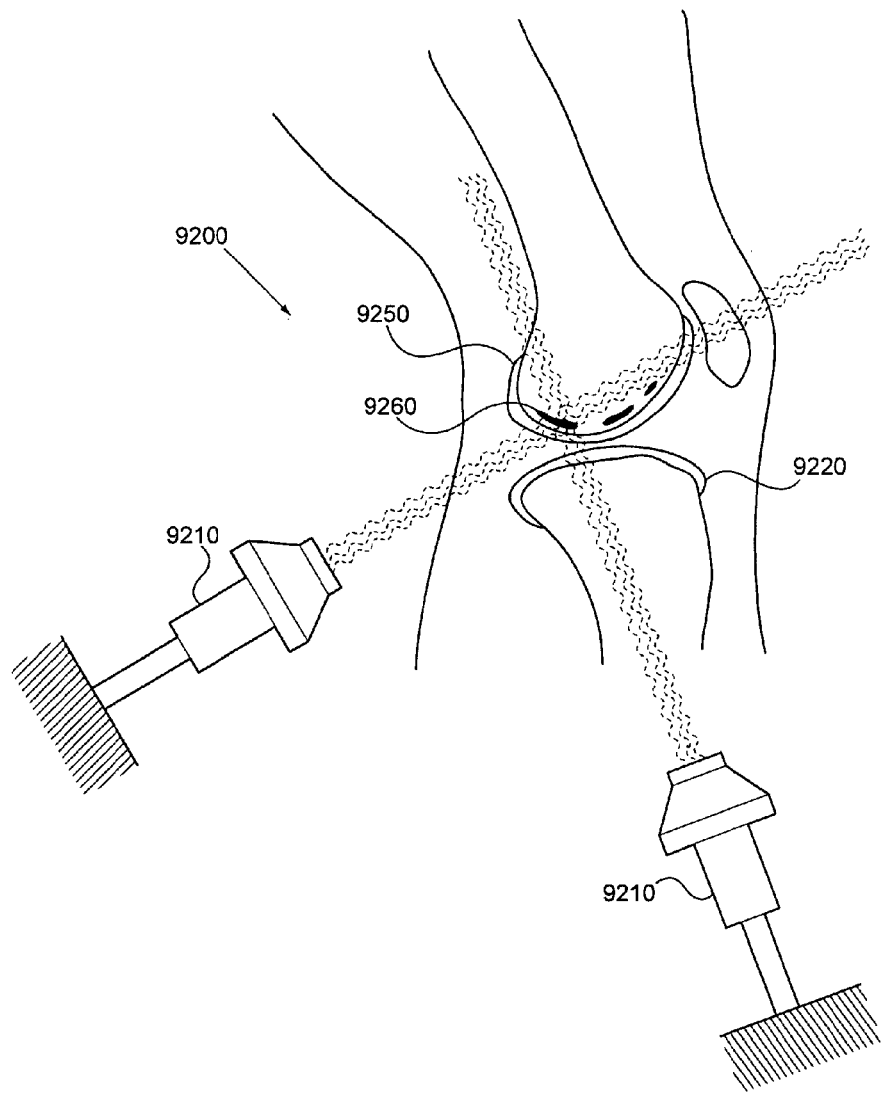
FIG. 22 depicts the application of focused energy to nerves surrounding the knee joint.

FIG. 22 depicts a peripheral joint 9200 being treated. Ultrasound transducer 9210 emits waves toward the knee joint to block nerves 9260 just underneath the bone periostium. Although a knee joint is depicted, it should be understood that many joints can be treated including small joints in the hand, intervertebral joints, the hip, the ankle, the wrist, and the shoulder.

Figure 23A:
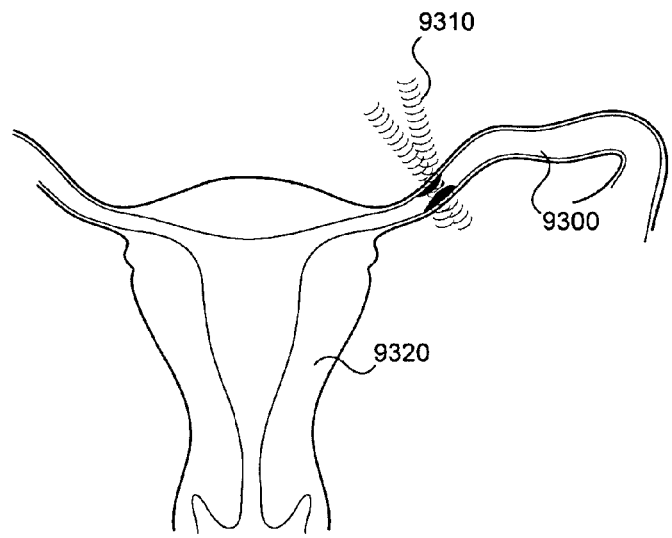
FIG. 23 depicts the application of energy to the fallopian tube to sterilize a patient.
Figure 23B:
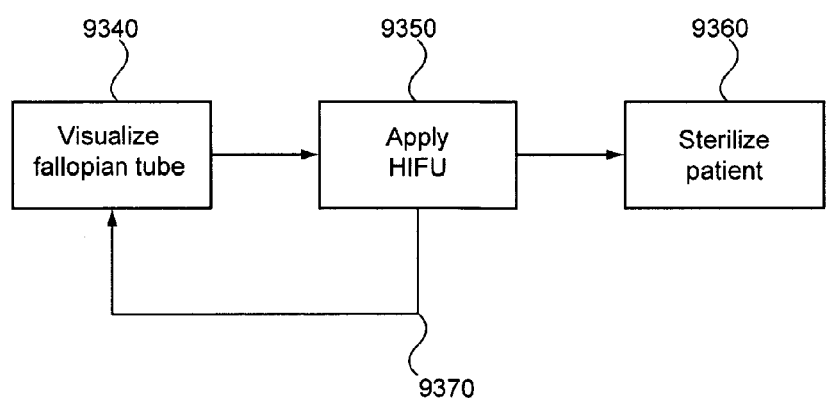
Figure 24:
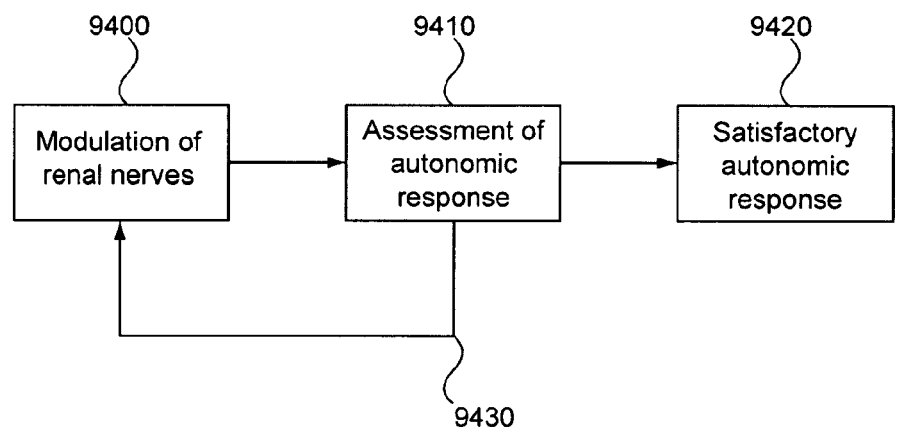
FIG. 24 depicts an algorithm to assess the effect of the neural modulation procedure on the autonomic nervous system. After a procedure is performed on the renal nerves, assessment of the autonomic response is performed by, for example, simulating the autonomic nervous system in one or more places.

FIG. 23a-b depicts closure of a fallopian tube 9300 of a uterus 9320 using externally applied ultrasound 9310 so as to prevent pregnancy. MRI or preferably ultrasound can be utilized for the imaging modality. Thermometry can be utilized as well so as to see the true ablation zone in real time. The fallopian tube 9300 can be visualized using ultrasound, MRI, CT scan or a laparoscope. Once the fallopian tube is targeted, external energy 9310, for example, ultrasound, can be utilized to close the fallopian tube to prevent pregnancy.

In other embodiments, ultrasound is applied to the uterus or fallopian tubes to aid in pregnancy by improving the receptivity of the sperm and/or egg for one another.

In 23b a method is depicted in which the fallopian tubes are visualized 9340 using MRI, CT, or ultrasound. HIFU 9350 is applied under visualization with MRI or ultrasound. As the fallopian tubes are heated, the collagen in the wall is heated until the walls of the fallopian tube close off. At this point the patient is sterilized 9360. During the treating time, it may be required to determine how effective the heating is progressing. If additional heat is required, then additional HIFU may be added to the fallopian tubes until there is closure of the tube and the patient is sterilized 9360.

The invention claimed is:

1. A method of treating a patient, comprising:
   directing an energy applicator within a blood vessel to a target region comprising a nerve within an autonomic nervous system and delivering a three dimensional pattern of unfocused ultrasound energy to the target region in an approximately spherical or ellipsoidal configuration around a reference position associated with the blood vessel using the energy applicator, wherein the energy applicator comprises an intravascular catheter.

2. The method of claim 1, wherein the blood vessel leads to or from a kidney.

3. The method of claim 1, wherein the nerve is up to ten millimeters away from the blood vessel.

4. The method of claim 1, wherein the delivery of ultrasound energy generates heat around the blood vessel but not inside a wall of the blood vessel.

5. The method of claim 4, wherein the delivery of ultrasound energy generates a temperature around the vessel between 40 and 60 degrees Fahrenheit.

6. The method of claim 4, wherein the delivery of ultrasound energy generates a temperature around the vessel between 60 and 90 degrees Fahrenheit.

7. The method of claim 4, wherein the method further comprises cooling the inside of the blood vessel.

8. The method of claim 1, wherein the intensity of the delivered ultrasound energy is between 50 mW/cm$^2$ and 1000 mW/cm$^2$.

9. The method of claim 1, wherein the frequency of the delivered ultrasound energy is between 0.5 Mhz and 10 Mhz.

10. The method of claim 1, wherein the nerve is a renal nerve.

11. The method of claim 1, wherein the delivered three dimensional pattern of unfocused ultrasound energy at least partially modulates nerves associated with the carotid sinus.

12. The method of claim 1, wherein the delivered three dimensional pattern of unfocused ultrasound energy at least partially ablates the carotid body.

13. The method of claim 1, wherein the nerve is associated with an aortic baroreceptor.

14. A method of altering the autonomic nervous system, comprising:
   delivering a three dimensional pattern of a first dose of unfocused ultrasound energy to a target region in the vicinity of a blood vessel within a patient; detecting a change in a parameter related to a response of the autonomic nervous system to the application of the first dose; and delivering a three dimensional pattern of a second dose of unfocused ultrasound energy to the target region in response to the detected change in the parameter,
   wherein the first and second doses of unfocused ultrasound energy are delivered to the target region in an approximately spherical or ellipsoidal configuration around a reference position associated with the blood vessel.

15. The method of claim 14, wherein the parameter comprises blood pressure.

16. The method of claim 14, wherein the parameter comprises a norepinephrine level in blood.

17. The method of claim 14, wherein the parameter comprises a norepinephrine level in a kidney.

18. The method of claim 14, wherein the parameter comprises a norepinephrine level in a blood vessel leading to a kidney.

19. The method of claim 14, wherein the parameter comprises a norepinephrine level in a blood vessel leading from a kidney.

20. The method of claim 14, further comprising creating a temperature map that represents an effect of heat generated by the second dose of ultrasound energy.

21. The method of claim 14, further comprising creating a map that represents tissue elasticity.

22. The method of claim 14, further comprising delivering a bioactive agent to a region surrounding the blood vessel prior to the application of ultrasound energy.

23. The method of claim 14, wherein the target region comprises a nerve.

24. The method of claim 23, wherein the nerve comprises a renal nerve.

25. The method of claim 23, wherein the nerve is associated with an aortic baroreceptor.

26. The method of claim 14, wherein the blood vessel is a renal artery or a renal vein.

27. The method of claim 14, wherein the blood vessel is a carotid artery.

28. The method of claim 14, wherein the three dimensional pattern of first and second doses of unfocused ultrasound energy are delivered to the carotid sinus to at least partially modulate the nerves associated with the carotid sinus.

29. The method of claim 14, wherein the three dimensional pattern of first and second doses of unfocused ultrasound energy are delivered to the carotid body to at least partially ablate the carotid body.

* * * * *